(12) United States Patent
Jain

(10) Patent No.: US 10,659,908 B2
(45) Date of Patent: *May 19, 2020

(54) SYSTEM AND METHOD TO CAPTURE IMAGE OF PINNA AND CHARACTERIZE HUMAN AUDITORY ANATOMY USING IMAGE OF PINNA

(71) Applicant: EmbodyVR, Inc., San Mateo, CA (US)

(72) Inventor: Kapil Jain, Redwood City, CA (US)

(73) Assignee: EmbodyVR, Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/542,930

(22) Filed: Aug. 16, 2019

(65) Prior Publication Data

US 2019/0379993 A1 Dec. 12, 2019

Related U.S. Application Data

(63) Continuation of application No. 15/811,441, filed on Nov. 13, 2017, now Pat. No. 10,433,095.

(Continued)

(51) Int. Cl.
*H04R 5/04* (2006.01)
*H04R 1/32* (2006.01)
(Continued)

(52) U.S. Cl.
CPC ............. *H04S 7/304* (2013.01); *A61B 5/121* (2013.01); *G01B 7/14* (2013.01); *G06K 9/00362* (2013.01); *G06K 9/66* (2013.01); *G06T 1/0007* (2013.01); *G06T 7/73* (2017.01); *G06T 7/80* (2017.01); *H04R 1/005* (2013.01); *H04R 1/1008* (2013.01); *H04R 1/1058* (2013.01); *H04R 1/22* (2013.01);
(Continued)

(58) Field of Classification Search
CPC ........ A61B 6/5217; G06T 7/80; H04R 1/005; H04R 1/32; H04R 1/323; H04R 1/1008; H04R 5/033; H04R 11/02; H04S 7/301; H04S 7/304; H04S 7/306; H04S 2400/11; H04S 2420/01
See application file for complete search history.

(56) References Cited

U.S. PATENT DOCUMENTS 5,708,725 A 1/1998 Ito
9,030,545 B2 * 5/2015 Pedersen ............ G06K 9/00362
348/77

(Continued)

FOREIGN PATENT DOCUMENTS

JP 3521900 B2 4/2004
KR 20150009384 A 1/2015
WO 2017047309 A1 3/2017

OTHER PUBLICATIONS

U.S. Appl. No. 15/811,295, Non-Final Office Action, dated Aug. 9, 2018, 13 pages.

(Continued)

*Primary Examiner* — Brian Ensey

(57) ABSTRACT

An image of a pinna is captured. Based on the image of the pinna, a non-linear transfer function is determined which characterizes how sound is transformed at the pinna. A signal is output indicative of one or more audio cues to facilitate spatial localization of sound via the pinna, where the one or more audio cues is based on the non-linear transfer function.

23 Claims, 23 Drawing Sheets

Related U.S. Application Data

(60) Provisional application No. 62/421,285, filed on Nov. 13, 2016, provisional application No. 62/421,380, filed on Nov. 14, 2016, provisional application No. 62/424,512, filed on Nov. 20, 2016, provisional application No. 62/466,268, filed on Mar. 2, 2017, provisional application No. 62/468,933, filed on Mar. 8, 2017.

(51) Int. Cl.

| | | |
|---|---|---|
| H04R 11/02 | (2006.01) | |
| H04S 7/00 | (2006.01) | |
| G01B 7/14 | (2006.01) | |
| H04S 3/00 | (2006.01) | |
| G06K 9/00 | (2006.01) | |
| G06T 7/80 | (2017.01) | |
| G06T 7/73 | (2017.01) | |
| G06K 9/66 | (2006.01) | |
| G06T 1/00 | (2006.01) | |
| H04R 1/00 | (2006.01) | |
| H04R 1/10 | (2006.01) | |
| H04R 3/04 | (2006.01) | |
| A61B 5/12 | (2006.01) | |
| H04R 1/22 | (2006.01) | |
| H04R 5/033 | (2006.01) | |
| A61B 5/00 | (2006.01) | |
| A61B 6/00 | (2006.01) | |

(52) U.S. Cl.
CPC .............. *H04R 1/32* (2013.01); *H04R 1/323* (2013.01); *H04R 3/04* (2013.01); *H04R 5/04* (2013.01); *H04S 3/008* (2013.01); *H04S 7/301* (2013.01); *H04S 7/306* (2013.01); *A61B 5/4005* (2013.01); *A61B 6/5217* (2013.01); *H04R 1/1016* (2013.01); *H04R 5/033* (2013.01); *H04R 11/02* (2013.01); *H04R 2201/029* (2013.01); *H04R 2225/77* (2013.01); *H04S 2400/11* (2013.01); *H04S 2420/01* (2013.01)

(56) References Cited

U.S. PATENT DOCUMENTS

| | | | |
|---|---|---|---|
| 9,473,858 | B2 | 10/2016 | Pedersen et al. |
| 9,544,706 | B1* | 1/2017 | Hirst ................. H04S 7/302 |
| 9,900,722 | B2 | 2/2018 | Bilinski et al. |
| 10,181,328 | B2 | 1/2019 | Jensen et al. |
| 10,200,806 | B2 | 2/2019 | Stein et al. |
| 2003/0035551 | A1 | 2/2003 | Light et al. |
| 2004/0136538 | A1 | 7/2004 | Cohen et al. |
| 2006/0067548 | A1 | 3/2006 | Slaney et al. |
| 2006/0193515 | A1 | 8/2006 | Kim et al. |
| 2006/0274901 | A1 | 12/2006 | Terai et al. |
| 2008/0107287 | A1 | 5/2008 | Beard |
| 2008/0175406 | A1 | 7/2008 | Smith |
| 2010/0215198 | A1 | 8/2010 | Ngia et al. |
| 2011/0009771 | A1 | 1/2011 | Guillon et al. |
| 2011/0206217 | A1 | 8/2011 | Weis |
| 2012/0183161 | A1 | 7/2012 | Agevik et al. |
| 2012/0328107 | A1 | 12/2012 | Nystrom et al. |
| 2013/0169779 | A1 | 7/2013 | Pedersen |
| 2013/0177166 | A1 | 7/2013 | Agevik et al. |
| 2013/0279724 | A1 | 10/2013 | Stafford et al. |
| 2014/0161412 | A1 | 6/2014 | Chase et al. |
| 2014/0270200 | A1 | 9/2014 | Usher et al. |
| 2015/0010160 | A1 | 1/2015 | Udesen |
| 2015/0172814 | A1 | 6/2015 | Usher et al. |
| 2016/0269849 | A1 | 9/2016 | Riggs et al. |
| 2017/0020382 | A1 | 1/2017 | Sezan et al. |
| 2017/0332186 | A1* | 11/2017 | Riggs ................. G06F 3/012 |
| 2018/0063652 | A1 | 3/2018 | Perkins et al. |
| 2018/0091921 | A1 | 3/2018 | Silva |

OTHER PUBLICATIONS

U.S. Appl. No. 15/811,295, Notice of Allowance, dated Feb. 27, 2019, 6 pages.
U.S. Appl. No. 15/811,392, Non-Final Rejection, dated Feb. 13, 2019, 9 pages.
U.S. Appl. No. 15/811,392, Notice of Allowance, dated May 30, 2019, 9 pages.
U.S. Appl. No. 15/811,642, Notice of Allowance, dated Sep. 11, 2018, 5 pages.
U.S. Appl. No. 16/138,931, Non-Final Rejection, dated Aug. 15, 2019, 13 pages.
International Application Serial No. PCT/2017/061413, International Search Report dated Mar. 5, 2018, 3 pages.
International Application Serial No. PCT/US2017/061417, International Search Report dated Mar. 5, 2018, 3 pages.
PCT Application Serial No. PCT/2018/052312, International Search Report dated Jan. 21, 2019, 3 pages.
U.S. Appl. No. 15/811,642, Non-Final Office Action dated Mar. 15, 2018, 5 pages.
International Application Serial No. PCT/2017/061413, Written Opinion dated Mar. 5, 2018, 5 pages.
U.S. Appl. No. 15/811,386, Notice of Allowance dated Feb. 5, 2018, 7 pages.
International Application Serial No. PCT/2018/052312, Written Opinion dated Jan. 21, 2019, 7 pages.
International Application Serial No. PCT/US2017/061417, Written Opinion dated Mar. 5, 2018, 8 pages.
Abaza, et al., "A Survey on Ear Biometrics", ACM Comput. Surv. 45, 2, Article 22, 2013, 35 pages.
Spagnol, et al., "Synthetic Individual Binaural Audio Delivery by Pinna Image Processing", International Journal of Pervasive Computing and Communications vol. 10 No. 3, 2014, pp. 239-254, Emerald Group Publishing Limited.

\* cited by examiner

SYSTEM AND METHOD TO CAPTURE IMAGE OF PINNA AND CHARACTERIZE HUMAN AUDITORY ANATOMY USING IMAGE OF PINNA

RELATED DISCLOSURES

This disclosure claims the benefit of priority under 35 U.S.C. § 120 of U.S. Non-Provisional application Ser. No. 15/811,441 filed Nov. 13, 2017 entitled "System and Method to Capture Image of Pinna and Characterize Human Auditory Anatomy Using Image of Pinna", which claims the benefit under 35 U.S.C. § 119(e) of U.S. Provisional Application No. 62/421,380 filed Nov. 14, 2016 entitled "Spatially Ambient Aware Audio Headset", U.S. Provisional Application No. 62/424,512 filed Nov. 20, 2016 entitled "Head Anatomy Measurement and HRTF Personalization", U.S. Provisional Application No. 62/468,933 filed Mar. 8, 2017 entitled "System and Method to Capture and Characterize Human Auditory Anatomy Using Mobile Device, U.S. Provisional Application No. 62/421,285 filed Nov. 13, 2016 entitled "Personalized Audio Reproduction System and Method", and U.S. Provisional Application No. 62/466,268 filed Mar. 2, 2017 entitled "Method and Protocol for Human Auditory Anatomy Characterization in Real Time", the contents each of which are herein incorporated by reference in their entireties.

This disclosure is also related to U.S. application Ser. No. 15/811,386, filed Nov. 13, 2017, entitled "Method, System, and Apparatus for Measuring Head Size Using a Magnetic Sensor Mounted on a Personal Audio Delivery Device", U.S. application Ser. No. 15/811,392, filed Nov. 13, 2017, entitled "Spatially Ambient Aware Personal Audio Delivery Device", U.S. application Ser. No. 15/811,295, filed Nov. 13, 2017, entitled "Image and Audio Based Characterization of a Human Auditory System for Personalized Audio Reproduction", and U.S. application Ser. No. 15/811,642, filed Nov. 13, 2017, entitled "Audio Based Characterization of a Human Auditory System for Personalized Audio Reproduction", the contents each of which are herein incorporated by reference in their entireties.

FIELD OF DISCLOSURE

The disclosure is related to consumer goods and, more particularly, to methods, systems, products, features, services, and other elements for characterizing a human auditory system of a person for personalized audio reproduction using personalized audio delivery devices such as headphones, hearables, speakers, earbuds, and hearing aids.

BACKGROUND

A human auditory system includes an outer ear, middle ear, and inner ear. With the outer ear, middle ear, and inner ear, the human auditory system is able to hear sound. For example, a sound source such as a loudspeaker in a room may output sound. A pinna of the outer ear receives the sound, directs the sound to an ear canal of the outer ear, which in turn directs the sound to the middle ear. The middle ear of the human auditory system transfers the sound into fluids of an inner ear for conversion into nerve impulses. A brain then interprets the nerve impulses to hear the sound. Further, the human auditory system is able to perceive the direction where the sound is coming from. The perception of direction of the sound source is based on interactions with human anatomy. The interaction includes the sound reflecting and/or reverberating and diffracting off a head, shoulder and pinna. The interaction generates audio cues which are decoded by the brain to perceive the direction where the sound is coming from.

It is now becoming more common to listen to sounds wearing personalized audio delivery devices such as headphones, hearables, earbuds, speakers, or hearing aids. The personalized audio delivery devices outputs sound, e.g., music, into the ear canal of the outer ear. For example, a user wears an earcup seated on the pinna which outputs the sound into the ear canal. Alternatively, a bone conduction headset vibrates middle ear bones to conduct the sound to the human auditory system. The personalized audio delivery devices accurately reproduce sound. But unlike sound from a sound source, the sound from the personalized audio delivery devices does not interact with the human anatomy such that direction where the sound is coming from is accurately perceptible. The seating of the earcup on the pinna prevents the sound from the personal audio delivery device from interacting with the pinna and the bone conduction may bypass the pinna altogether. Audio cues indicative of direction is not generated and as a result the person is not able to perceive the direction where the sound is coming from.

BRIEF DESCRIPTION OF THE DRAWINGS

Features, aspects, and advantages of the presently disclosed technology may be better understood with regard to the following description, appended claims, and accompanying drawings where:

Figure 1:
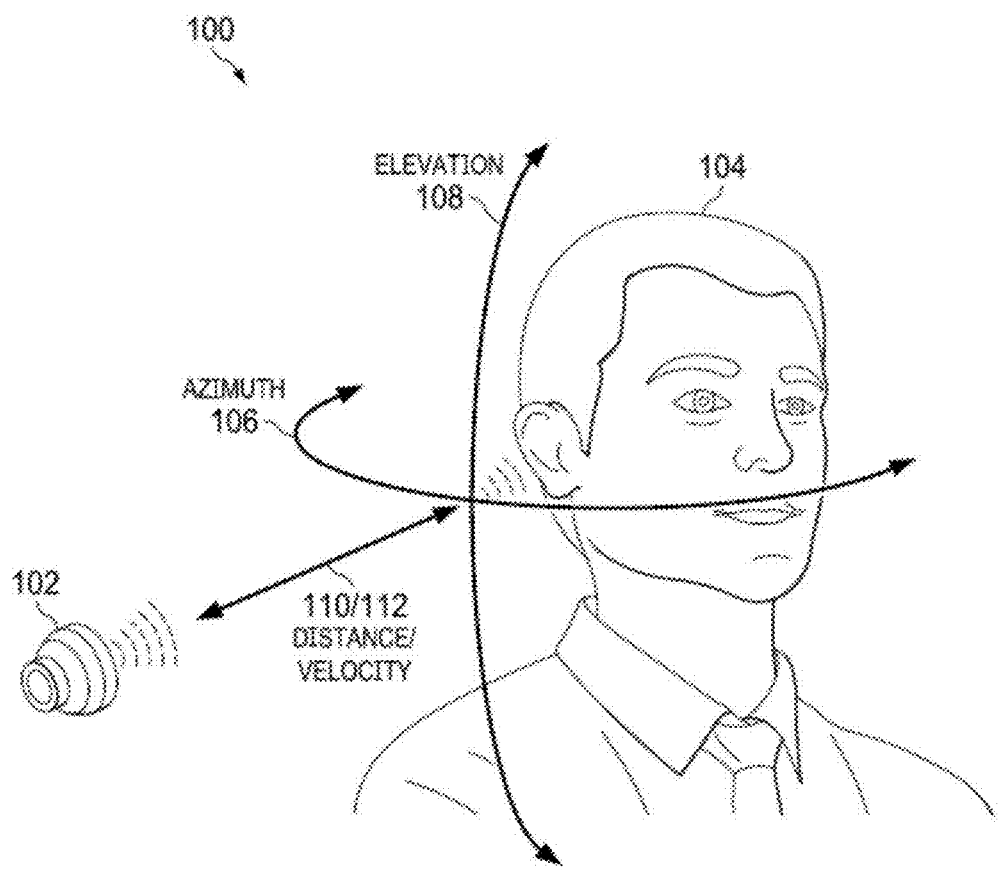
FIG. 1 shows an example visualization of various parameters used for spatial localization of sound.

The drawings are for the purpose of illustrating example embodiments, but it is understood that the embodiments are not limited to the arrangements and instrumentality shown in the drawings.

DETAILED DESCRIPTION

A sound source may output sound. A direction where the sound comes from may be identified by the human auditory system using one or more audio cues. The audio cues may be sound (e.g., reflections and reverberations) indicative of a spatial location of the sound, e.g., where the sound is coming from. The audio cues may be generated from interactions between the sound, objects in an environment, and human anatomy before reaching the human auditory system. For example, reverberation and reflection from the objects may generate audio cues. Additionally, or alternatively, aspects of the human anatomy such as head shape, head size, shoulder shape, shoulder size, and outer ear (pinna) structure may generate audio cues. Each person may have different human anatomy. In this regard, the audio cues used by one person to spatially localize the sound may be different for another person.

FIG. 1 is an example visualization 100 of parameters which facilitates spatially localizing sound output by a sound source 102. One or more parameters may describe a relationship between a position of a listener 104 and the sound source 102. The parameters may include an azimuth 106, elevation 108, distance 110, and velocity 112. The azimuth 106 may be an angle in a horizontal plane between the listener 104 and the sound source 102. The elevation 108 may be an angle in a vertical plane between the listener 104 and the sound source 102. The distance 110 may be a separation between the listener 104 and the sound source 102. The velocity 110 may be a rate of movement of the sound source 102, respectively. Other parameters indicative of location may also be used to describe a location of the sound source 102.

Figure 2:
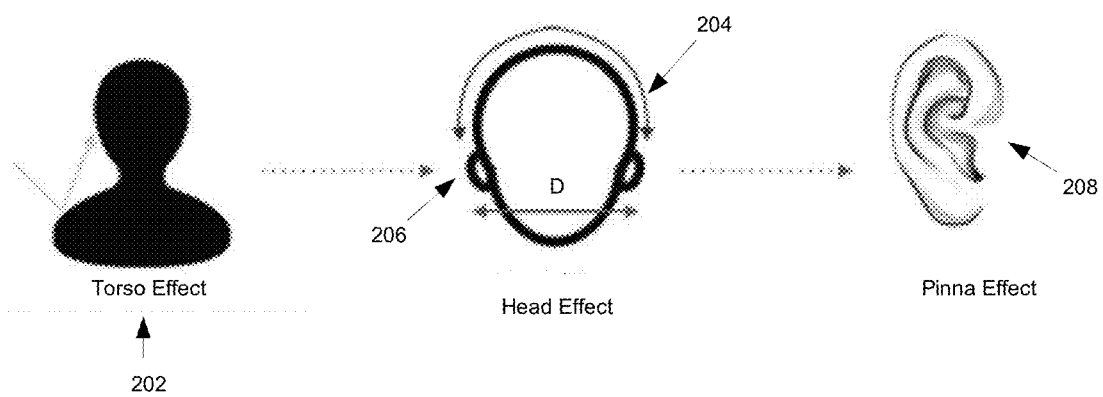
FIG. 2 shows aspects of a human anatomy in spatial localization of sound.

FIG. 2 shows aspects of a human anatomy 202-208 used in sound localization. Audio cues may be generated based on the interaction of sound with the human anatomy. The audio cues may be indicative of a spatial location from where the sound comes from. The human anatomy which is illustrated includes a torso 202, head 204 with ears 206, and a pinna 208.

Reflections of sound from the torso 202 may generate an audio cue indicative of elevation and distance from where the sound is coming from, e.g., the sound source. These reflections are modeled as torso effect. Overall shape of the head 204 including ear symmetry and distance D between the ears 206 may generate an audio cue regarding azimuth and elevation from where the sound is coming from. This is modeled as head effect. Finally, how sound interacts with the shape, size, and structure of the pinna 208 may generate an audio cue regarding elevation, distance and velocity from where the sound is coming from.

Figure 3:
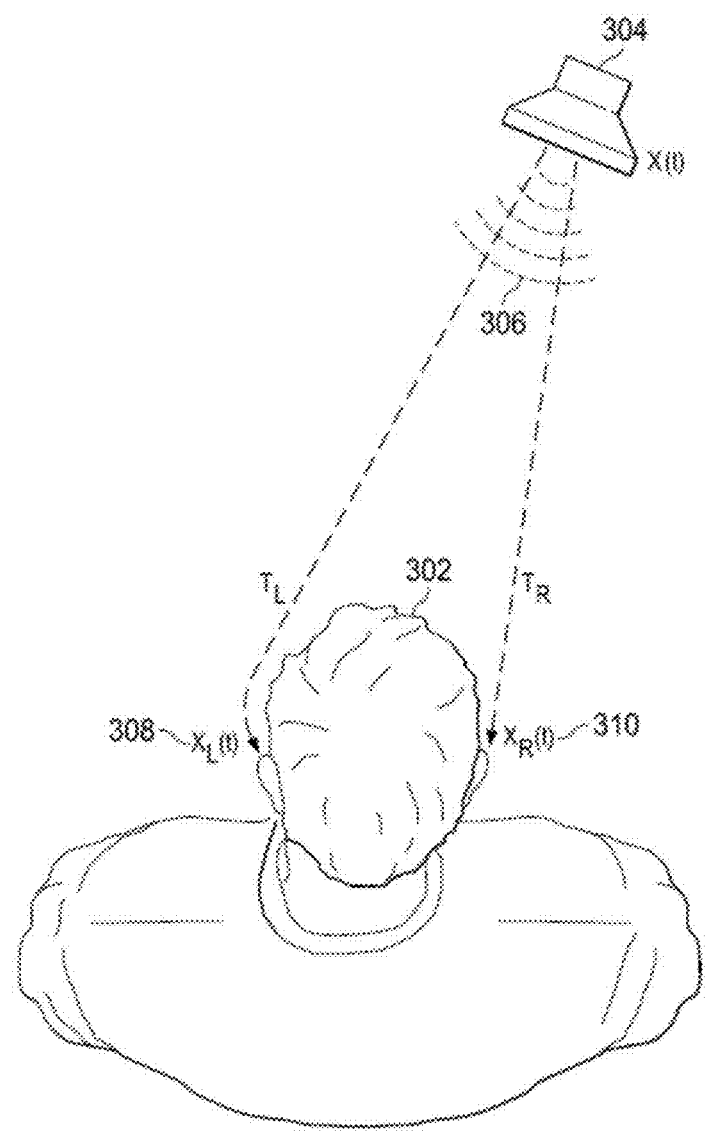
FIG. 3 show examples of an effect of human anatomy on interaural audio cues.

FIG. 3 shows how the audio cue indicative of azimuth is generated. A person 302 may be located a certain distance away from a sound source 304. The sound source 304 may output sound 306 which is then perceived by the person at a left ear 308 and a right ear 310.

An interaural time difference (ITD) represents a difference in time arrival between the two ears 308, 310. Sound 306 generated by sound source 304, x(t), takes $T_L$ amount of time to reach the left ear 308 and $T_R$ amount of time to reach the right ear 310. ITD represents difference between $T_L$ and $T_R$. Similarly, at any time t, sound pressure level at left ear 308 $X_L(t)$ is different from the one experienced at right ear 310 $X_R(t)$. This difference in intensity is represented by an interaural level difference (ILD) audio cue. These audio cues (ITD and ILD) may be different for a different shape and size of head. A bigger head i.e. larger distance between left and right ear 308, 310, will generate larger time and intensity difference than a smaller head.

The ITD and ILD audio cues may be directly proportional to the azimuth between the listener and the sound source. In this regard, azimuth of the sound source may be perceived. ITD and ILD, however, may be insufficient to further localize the direction of the sound in terms of elevation, distance and velocity of the sound source.

Figure 4:
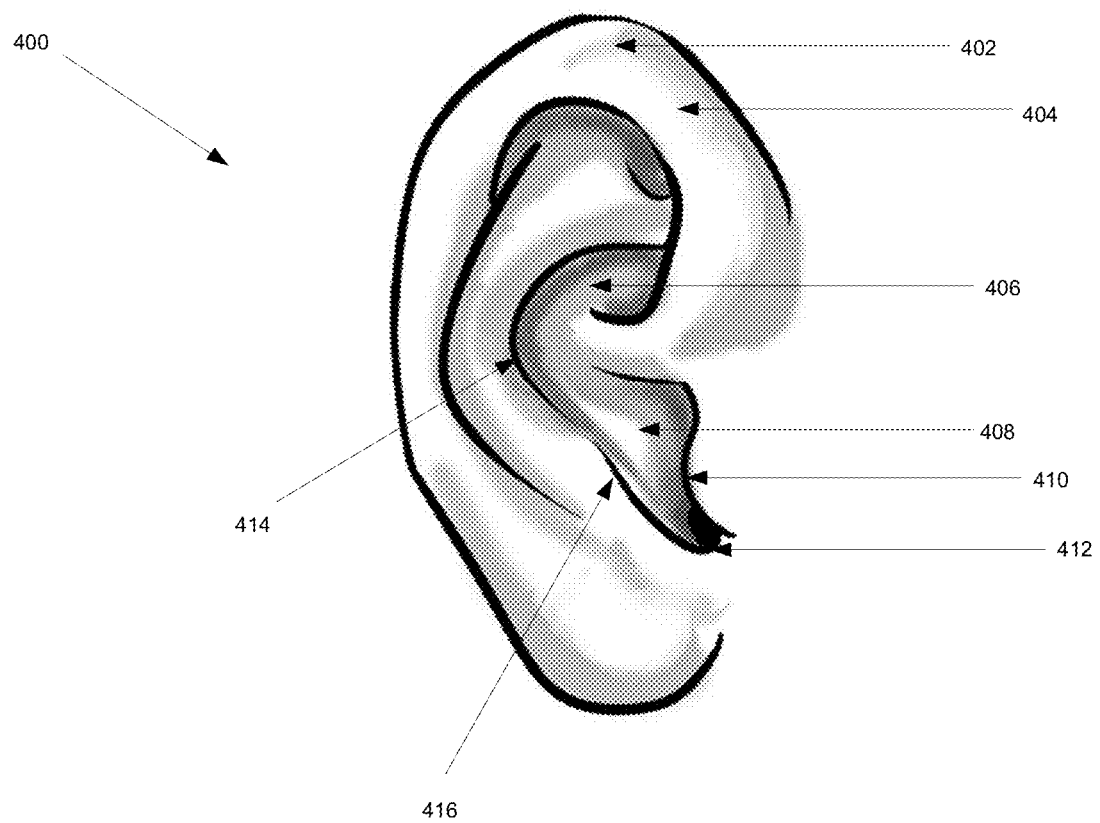
FIG. 4 shows a detailed view of a pinna of the human anatomy.

FIG. 4 shows a detailed view of an anatomy of a pinna 400 and how the sound may be transformed. The pinna 400 may have various features. The features may include a height, width, shape, and depth of the pinna 400. Additionally, the features may include a helix 402, fossa 404, cymba conchae 406, cavum conche 408, tragus 410, ear notch 412, antihelix 414, and antitragus 416 among other features. The features form one or more cavities within which sound may resonant and/or reflect. For example, an amplitude of sound from a sound source may be increased at certain frequencies and decreased at other frequencies due to the structure of the pinna. The increase and/or decrease may be due to the reflection and/or reverberations associated with features of the pinna 400. The transformation of the sound may generate audio cues. In turn, these audio cues may be used to further localize the sound source in terms of the elevation, distance, and velocity.

Personal audio delivery devices such as headphones, hearables, speakers, and hearing aids may output sound directly into the human auditory system. For example, an earcup of a headphone may be placed on the pinna and a transducer in the earcup may output sound into an ear canal of the human auditory system. However, the earcup may cover or partially cover the pinna. As a result, spatial localization of any sound may be impaired. The pinna might not interact with such sounds so as to generate audio cues to perceive the direction where the sound is coming from. Similar issues may exist for personal audio delivery systems in the form of bone conduction headsets. Bone conduction headsets may bypass the outer ear (pinna) all together, resulting in the pinna not generating audio cues.

In this case, the audio cues may be artificially generated to facilitate spatial localization in terms of elevation, distance and velocity. A non-linear transfer function, e.g., also referred to as a head related transfer function (HRTF), may facilitate generating the audio cues. The non-linear transfer function may characterize how sound is received by a human auditory system based on interaction with the pinna. The non-linear transfer function may be used to artificially generate the audio cues for determining azimuth, elevation, distance and/or velocity of a sound source.

Each person may have differences in pinna, and similarly head size and torso. As a result, the non-linear transfer function for one user cannot be used for another user. Such a use would result in audio cues being generated such that the sound source is perceived coming from a different spatial location from where it is intended to be perceived.

Embodiments described herein are directed to a method, system, and apparatus for characterizing a pinna of an individual to facilitate generating a non-linear transfer function for the individual. The non-linear transfer function may define how sound is transformed by the pinna for the individual. In turn, the non-linear transfer function may be used to artificially generate audio cues for spatializing sound both output and not output by the personal audio delivery device. With spatialization, the individual may be given a perception of sound coming from a certain direction, e.g., azimuth, elevation, distance and/or velocity, thereby improving the individual's experience with the personal audio delivery device in applications such as listening to music, virtual reality, and augmented virtual reality.

Figure 5:
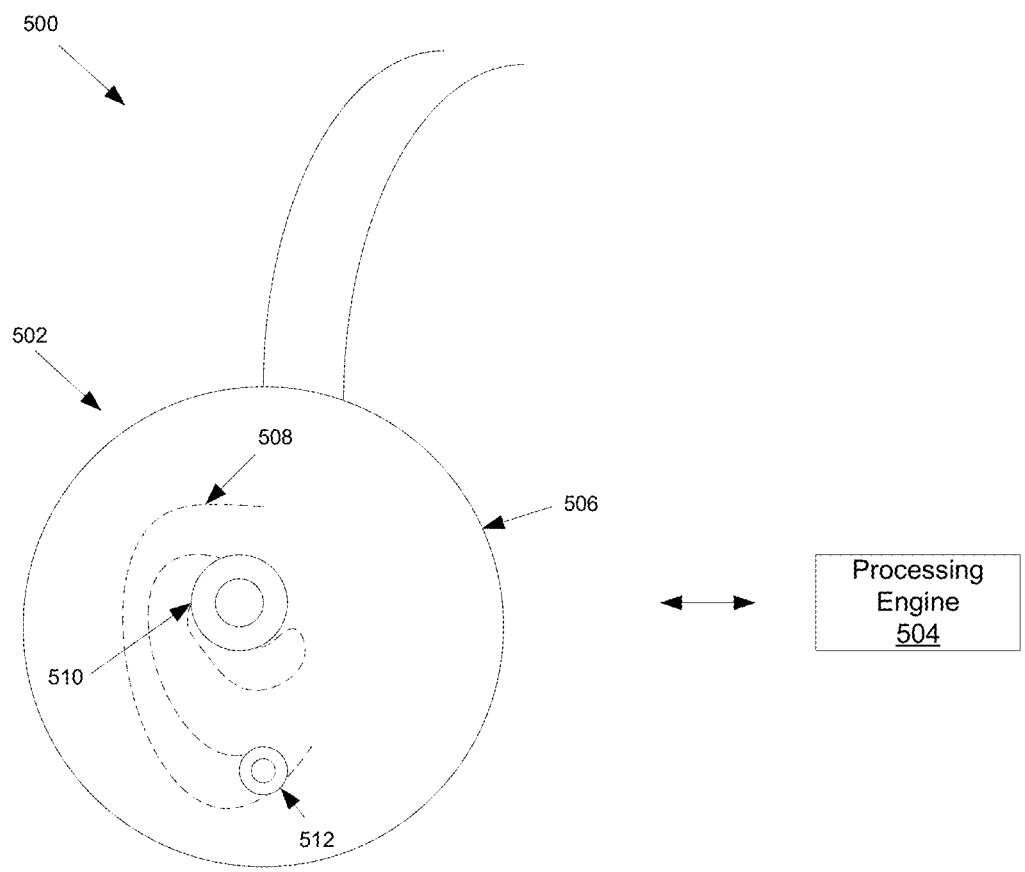
FIG. 5 shows an example system for personalizing audio reproduction.

FIG. 5 illustrates an example system 500 for personalizing audio reproduction. The system 500 may include the personal audio delivery device 502 and a processing engine 504.

The personal audio delivery device 502 may be a headphone, hearable, or hearing aid for playing audio. The personal audio delivery device 502 may have an earcup 506 which is worn on a pinna 508. The pinna 508 may not be visible externally when the earcup 506 is worn, but pinna 508 is shown as visible for purposes of illustration. The earcup 506 may have one or more transducers 510 and one or more sensors 512. The one or more transducers 510 may be speakers which output audible sound based on conversion of an electrical signal representative of the sound. A sensor 512 may take the form of a microphone, image sensor, and/or motion sensor among others. The one or more transducers 510 and/or one or more sensors 512 may be positioned within an earcup of the personal audio delivery device. The processing engine may process the signal associated with the one or more transducers and/or sensors.

Figure 6A:
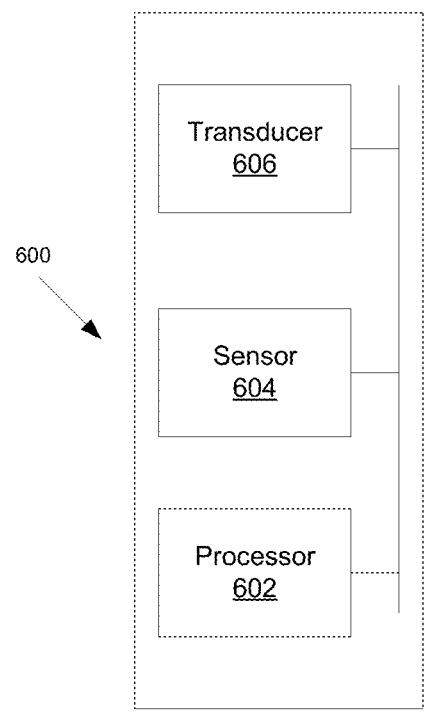
FIGS. 6A and 6B show example arrangements of the processing engine in the example system for personalizing audio reproduction.
Figure 6B:
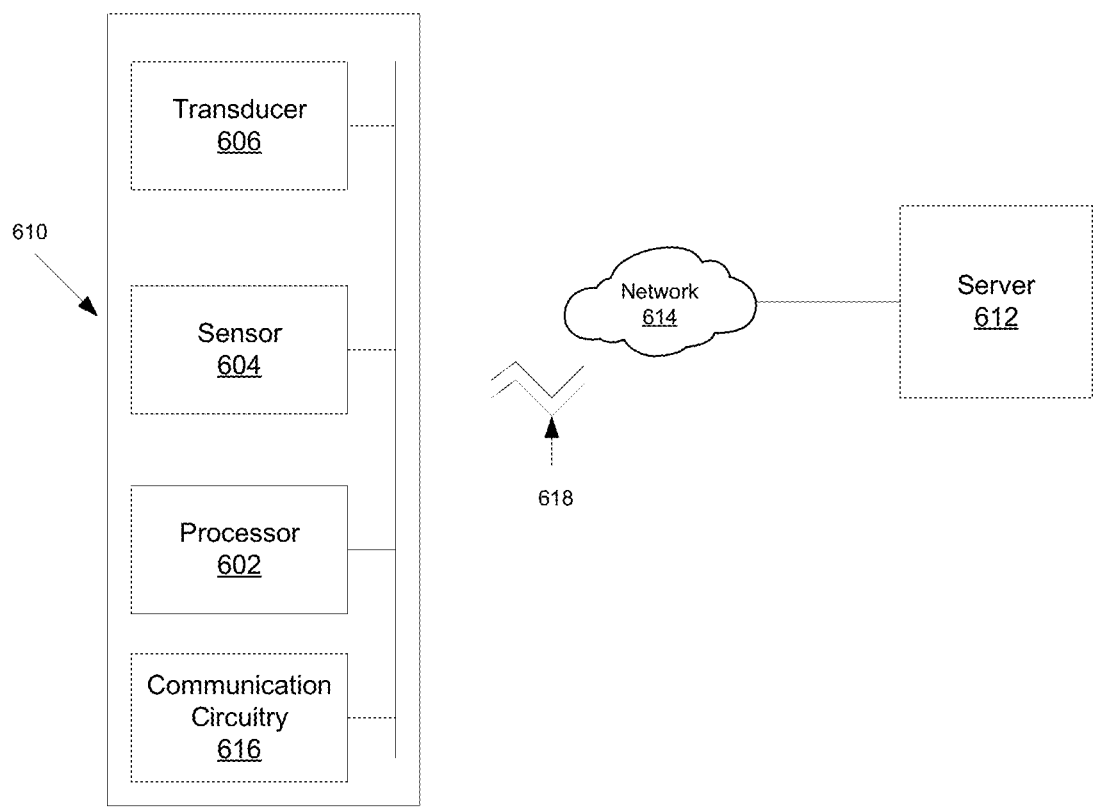

FIGS. 6A and 6B show example arrangements of the processing engine in the example system for spatial localization. The processing engine may take the form of a processor or a server, among other arrangements.

FIG. 6A shows an arrangement of a personal audio delivery device 600 with a processing engine in the form of the processor 602. The processor 602 may be a central processing unit (CPU) local to the personal audio delivery device 600 which executes computer instructions stored in storage such as memory to process the signals associated with the one or more sensors 604 and one or more transducers 606. The processor 602 may be local when the processor 602 is integrated with the personal audio delivery device 600.

FIG. 6B shows an arrangement of a personal audio delivery device 610 and a processing engine in the form of a server 612 coupled via a network 614. The server 612 may be a network based computing system. The server 612 may process the signals associated with the one or more sensors 604 and one or more transducers 606. The server 612 may be accessible to the personal audio delivery device via the network 614. The network 614 may take the form of a wired or wireless network. The personal audio delivery device 612 may have communication circuitry 616 for communicating signals 618 with the server 612, e.g., via WiFi or Ethernet, to facilitate processing of signals associated with the transducers and/or sensors.

Latency associated with processing the signals associated with the transducers and/or sensors may be less with the system having the local processor as compared to the system with the server. The latency may be less because there is no delay associated with communication to the server. The personal audio delivery device may be powered by a battery. Processing signals on the local processor may reduce how long a personal audio delivery device may operate before the battery source needs to be charged or replaced. The processing of the signals associated with the sound output by the one or more transducers and/or one or more sensors may consume power from the battery which otherwise would be used by the personal audio delivery device to output sound.

The system for spatial localization may take other forms as well. For example, the processing engine may take the form of the CPU local to the personal audio delivery device and the server. In other words, the processing of the signals may be performed locally by the processor at the personal audio delivery device as well as remotely at the server. Yet other variations are also possible.

Figure 7:
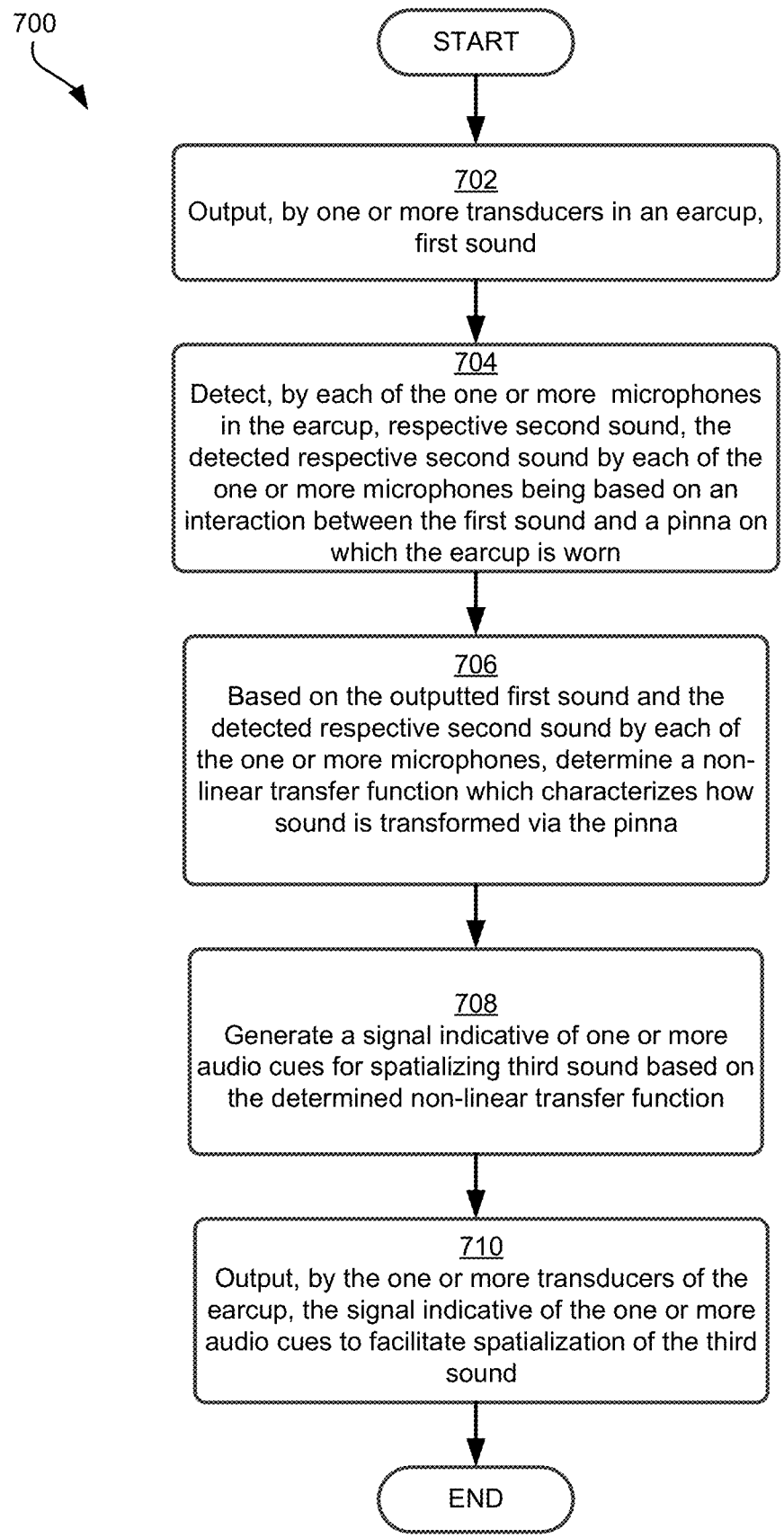
FIG. 7 is an example flow chart of functions associated with a sound-based method for personalizing audio reproduction.

FIG. 7 is a flow chart of functions 700 associated with a sound-based method for personalizing audio reproduction. These functions may be performed by the example system which includes the personal audio delivery device and processing engine.

Briefly, at 702, a first sound may be output by one or more transducers in an earcup worn on a pinna. At 704, each of one or more microphones in the earcup may detect respective second sound. The detected respective second sound by each of the one or more microphones may be based on an interaction between the first audio sound and the pinna on which the earcup is worn. At 706, based on the first audio sound and the detected respective sound by each of the one or more microphones, a non-linear transfer function is determined which characterizes how the first sound is transformed via the pinna. At 708, a signal indicative of one or more audio cues may be generated for third sound based on the determined non-linear transfer function. At 710, the signal indicative of the one or more audio cues is output by the one or more transducers in the earcup to facilitate spatial localization of the third sound.

Methods and the other process disclosed herein may include one or more operations, functions, or actions. Although the blocks are illustrated in sequential order, these blocks may also be performed in parallel, and/or in a different order than those described herein. Also, the various blocks may be combined into fewer blocks, divided into additional blocks, and/or removed based upon the desired implementation.

In addition, for the methods and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device. In addition, each block in the FIG.s may represent circuitry that is wired to perform the specific logical functions in the process.

An individual may wear a personal audio delivery device. The personal audio delivery device may have an earcup which the individual wears on a pinna. At 702, a first sound may be output by one or more transducers in the earcup worn on the pinna. A signal indicative of the first sound may be provided by the processing engine to the one or more transducers and the one or more transducers in the earcup may output the first sound based on the signal. The first sound may take a variety of forms. For example, the first sound may take the form of a chirp with varying frequency in an audible range of a human, i.e., 20 Hz to 20 kHz. Other sounds may also be used bandlimited between 20 Hz to 20 kHz.

As the first sound is output, the first sound reflects and resonates within features of the pinna creating audio scatter. At 704, each sensor of one or more sensors in the earcup may detect respective second sound. Each sensor may be a microphone. The detected respective second sound by each of the one or more microphones may be a frequency response of a pinna on which the earcup is worn at a location of the sensor caused by an interaction between the first audio sound and the pinna. The first sound output by the transducer may have been chosen so that the detected respective second sound of each of the one or more microphones uniquely characterizes the pinna.

Figure 8:
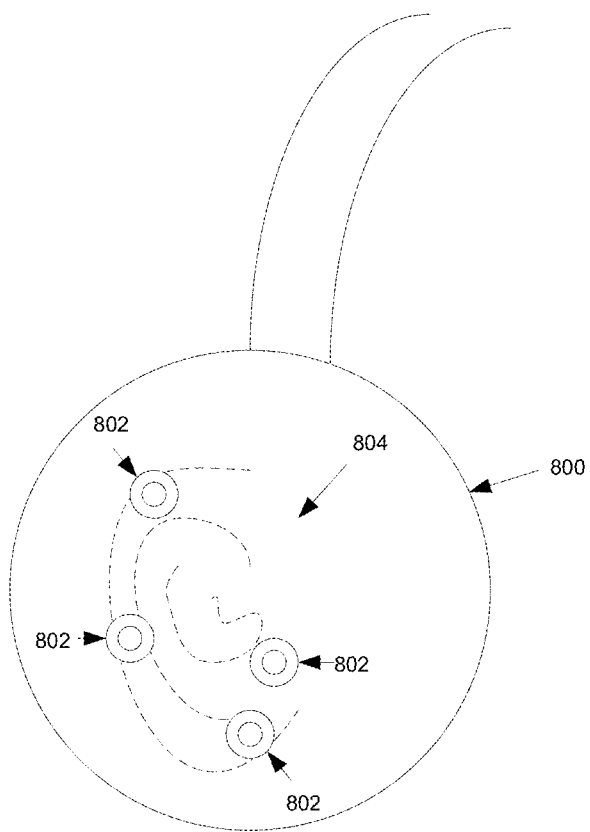
FIG. 8 shows an example earcup for detecting sound.

FIG. 8 shows an example earcup 800 for detecting the respective second sound. The earcup 800 may have one or more microphones 802 located at specific locations around a pinna 804 such that audio scatter detected by each microphone uniquely characterizes the pinna 804. For example, the earcup 800 may have four microphones 802 located at four specific features of the pinna, such as the fossa, cymba conchae, cavum conchae, and ear notch. Each microphone may detect respective second sound. The detected respective second sound may be indicative of a frequency response of the pinna at the location of the microphone. The detected respective second sound by each of the one or more microphones may be sent to the processing engine.

At 706, based on the first sound and the detected respective second sound of each of the one or more microphones, a non-linear transfer function is determined which characterizes how the first sound is transformed via the pinna.

Figure 9:
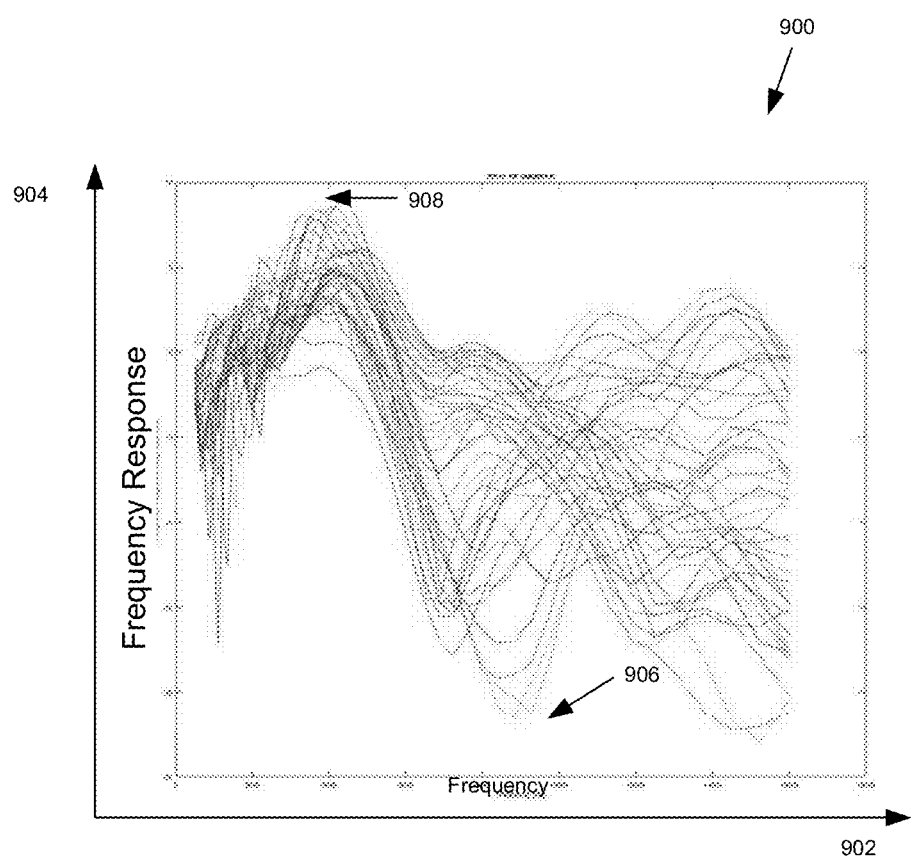
FIG. 9 shows an example of a non-linear transfer function.

FIG. 9 shows an example of the non-linear transfer function 900 for generating the missing audio cues. A horizontal axis 902 may represent a frequency heard at a pinna, e.g., in Hz, while a vertical axis 904 may represent a frequency response, e.g., in dB. The non-linear transfer function may characterize how a pinna transforms sound. For example, the non-linear transfer function shown in FIG. 9 may define waveforms indicative of frequency responses of the pinna at different elevations of the sound source. For example, each waveform may be associated with a particular elevation of the sound source. Further, each waveform may be associated with a same azimuth of a sound source. In this regard, waveforms for a given elevation and azimuth may define the frequency response of the pinna of that particular user when sound comes from the given elevation and azimuth. Further, regions 906 may represent notches and regions 908 may represent peaks in the frequency response of the pinna.

Figure 10A:
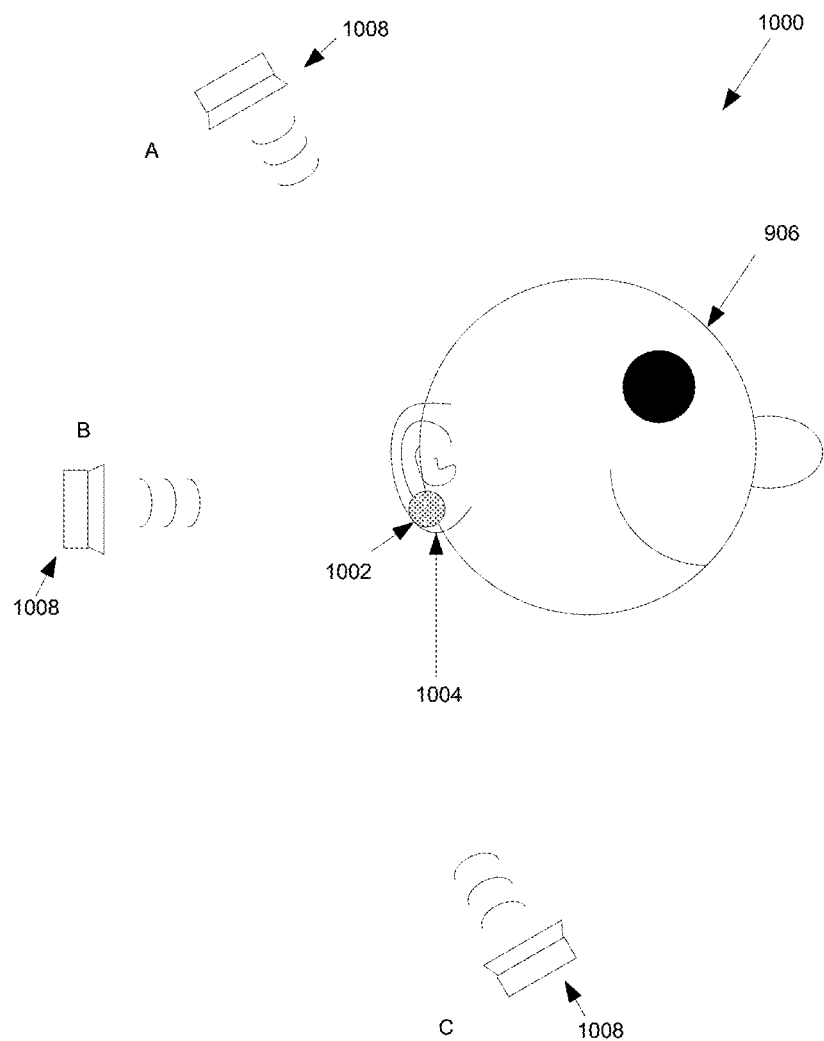
FIGS. 10A-C illustrate example arrangements associated with determining a non-linear transfer function.
Figure 10B:
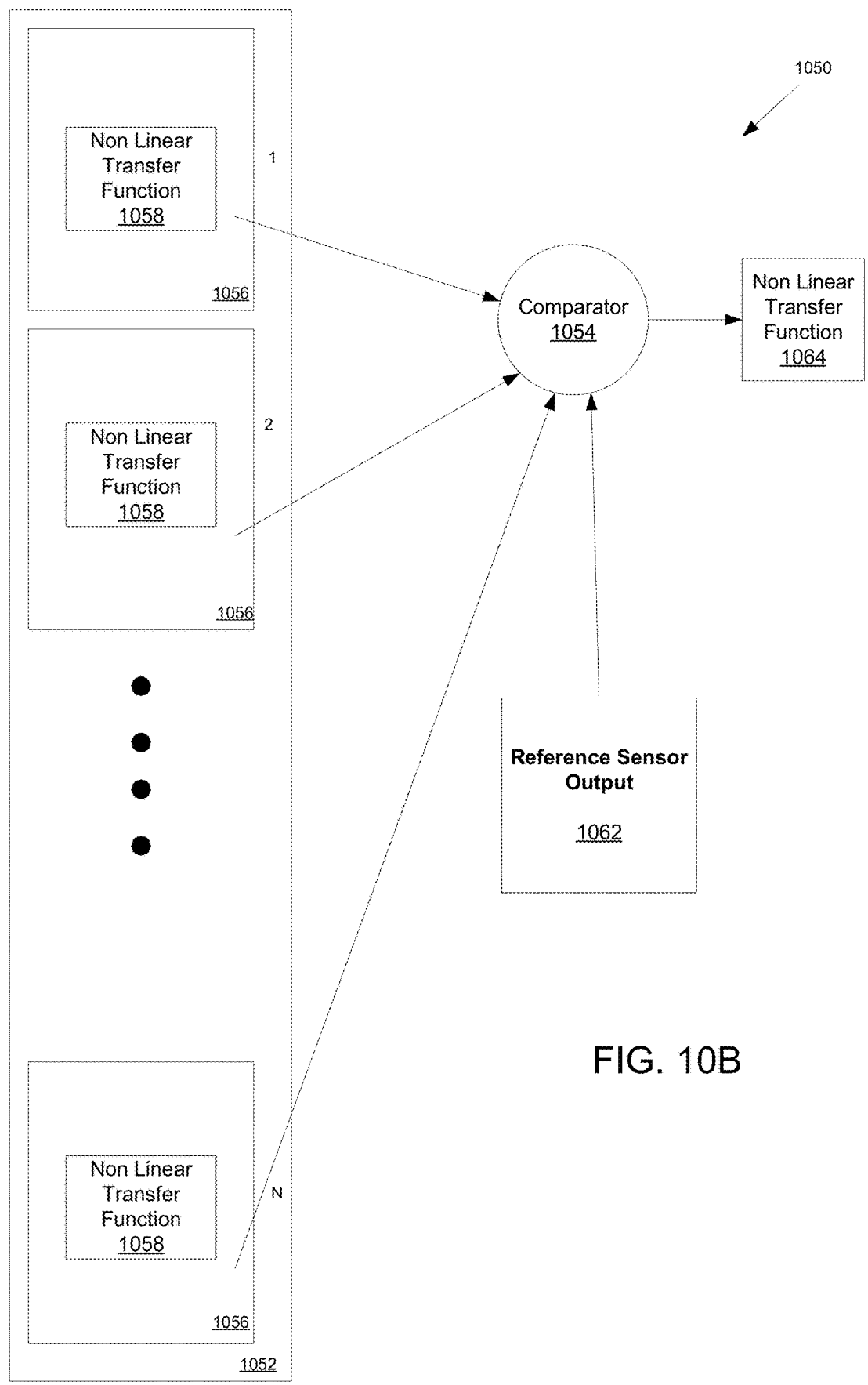
Figure 10C:
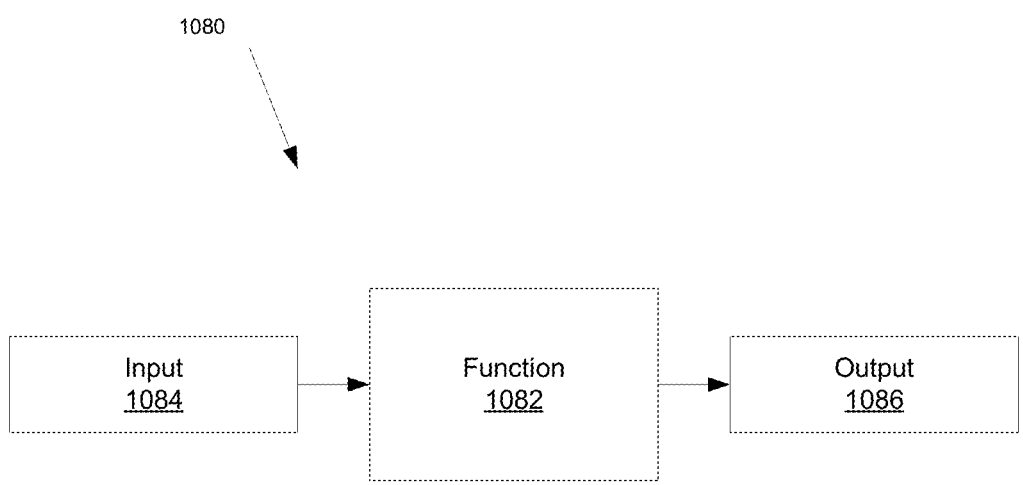

FIGS. 10A-C illustrate example arrangements associated with determining the non-linear transfer function.

A direct measurement may be performed during a learning process for each of a plurality of individuals different from the individual for whom the second sound is detected at step 704. The direct measurement for each of the plurality of individuals may result in determining a plurality of non-linear transfer functions.

FIG. 10A illustrates an example arrangement 1000 associated with determining the non-linear transfer function via the direct measurement. A microphone 1002 may be placed in a pinna 1004 of an individual 1006. The individual 1006 may different for whom the second sound is detected at 704. Then, a sound source 1008 may be moved around the individual 1006. The sound source 1008 may be moved to a plurality of spatial locations in azimuth, elevation, distance, and/or velocity around the individual, examples which are shown as positions A, B, and C. At each location, the sound source 1008 may output sound which may take the form of an impulse. Additionally, or alternatively, the sound source may be a chirp with varying frequency in an audible range of a human, i.e., 20 Hz to 20 kHz. Other sounds may also be used bandlimited between 20 Hz to 20 kHz. Frequency responses of the pinna 1004 measured by the microphone 1002 in the pinna 1004 for the plurality of spatial locations may be indicative of the non-linear transfer function for the pinna 1004. In some cases, a plurality of non-linear transfer functions may be determined. Each of the plurality of non-linear transfer functions may describe one or more of frequency responses of the pinna versus elevation for a given azimuth, frequency responses of the pinna versus distance for a given azimuth, and/or frequency responses of the pinna versus velocity for a given azimuth. The non-linear transfer function may be unique to the individual 1006 such that a direct measurement performed for the pinna 1002 of another individual would result in a different non-linear transfer function. In this regard, the non-linear transfer functions for a plurality of individuals may be determined and stored, e.g., in a database.

FIG. 10B illustrates an example arrangement 1050 for determining the non-linear transfer function at step 706. The non-linear transfer function may be based on the plurality of non-linear transfer functions determined during the learning process.

The example arrangement 1050 may include a database 1052 and comparator 1054. The database 1052 and comparator 1054 may reside on the personal audio delivery device, server, or some other device. The database 1052 may store the plurality of non-linear transfer functions determined during the learning process. An entry 1056 in the database 1052 may define a respective non-linear transfer function 1058 of the plurality of non-linear transfer functions during the learning process. The database may have a plurality of entries 1:N. The example arrangement may also include a reference sensor output 1062.

The reference sensor output 1062 may be indicative of one or more frequency responses of the pinna for the individual for whom the audio cues is to be generated. For example, the reference sensor output 1062 may be the detected respective second sound by each of the one or more microphones at step 704. If the earcup has four microphones, then the reference sensor output 1062 may include at least four detected respective second sound corresponding to the locations of the four microphones. The comparator 1054 may be arranged to compare the frequency responses of each non-linear transfer function 1058 to the detected respective second sound by the one or more microphones associated with the reference sensor output 1062 to identify a non-linear transfer function in the entries 1:N which is close (e.g., similar) to the reference sensor output 1062.

For example, the frequency responses of the pinna associated with non-linear transfer function 1058 may be compared with the detected respective second sound of each of the one or more microphones associated with step 704 (reference sensor output 1062) to identify the non-linear transfer function 1064 which has frequency responses that closely matches the reference sensor output 1062. The closeness of match may be based on a distance between one or more of the frequency responses of the pinna associated with non-linear transfer function 1058 and the detected respective second sound of each of the one or more microphones, among other measures. The comparator 1054 may output a non-linear transfer function 1064 associated with the closeness (e.g., a closest match). For instance, the non-linear transfer function 1064 may be a non-linear transfer function 1058 whose frequency responses most closely matches the reference sensor output 1062. In this regard, the direct measurement may not need to be performed on the pinna of the individual to determine the non-linear transfer function 1064. Instead, the non-linear transfer function 1064 may be based on the plurality of non-linear transfer functions determined during the learning process and stored and the database 1052 and used in real time to determine the non-linear transfer function 1064.

In another example, the non-linear transfer function 1064 for the individual for whom the second sound is detected at 706 may be based on a combination of one or more of the plurality of non-linear transfer functions determined during the learning process. For instance, one or more of the plurality of non-linear transfer functions may be weighed to determine non-linear transfer function for the individual for whom the second sound is detected at 704. The weighting may be based on a classification, e.g., closeness or similarity of match, between the frequency responses associated with the reference sensor output 1062 of step 706 and the frequency responses of the non-linear transfer function 1058 of the plurality of non-linear transfer functions. For instance, a closer match may result in a stronger weighting while a farther match may result in a weaker weighting. Then, the weighed non-linear transfer functions may be combined, e.g., summed, to form the non-linear transfer function 1062 associated with step 706.

FIG. 10C illustrates another example arrangement 1080 for determining the non-linear transfer function at step 704. The plurality of non-linear transfer functions and associated sensor outputs determined during the learning process may be parameterized via numerical analysis methods to define a function 1082 with an input 1084 and output 1086. The input 1084 to the function 1082 may be a sensor output and the output 1086 of the function 1082 may be a non-linear transfer function for the sensor output. The functions may take a variety of forms.

For instance, the function 1082 may take the form of a model fit to the plurality of non-linear transfer functions determined during the learning phase using well known data fitting techniques such as neural networks. A sensor output may be input into the model and the model may output a non-linear transfer function for sensor output. The sensor output may be detected respective second sound by each of the one or more microphones associated with step 704. The output may be the non-linear transfer function associated with step 706.

In some examples, the non-linear transfer function associated with step 706 may be stored, e.g., in memory. In this regard, a process for determining the non-linear transfer function may be personalized to a user and need to be determined one-time and used as described below.

At 708, a signal indicative of one or more audio cues may be generated for third sound based on the determined non-linear transfer function. For example, the identified non-linear transfer function may be modulated with a sound signal associated with the third sound to form the signal indicative of one or more audio cues. The non-linear transfer function may be an impulse response which is convolved with the sound signal in a time domain or multiplied with the first signal in a frequency domain to generate the signal indicative of the one or more audio cues. The sound signal may represent the third sound such as music or voice or sound output from a sound source external to the personal audio delivery device which does not interact with the pinna. As a result, audio cues associated with spatial location of the third sound may be missing. The modulation of the sound signal with the non-linear transfer may result in artificially generating these missing audio cues in the form of the signal indicative of the one or more audio cues.

The modulation process may be now described in more detail for spatializing sound. A direction may be associated with the third sound to be spatialized. For example, metadata associated with the third sound may define a given azimuth and elevation for which the third sound is to be perceived. A frequency response of the non-linear transfer function associated with the direction may be modulated with a sound signal associated with the third sound to generate a signal indicative of one or more audio cues that facilitate spatialization of the third sound. For example, non-linear transfer function may define waveforms indicative of a frequency response of the pinna when sound comes from the given azimuth and elevation. These waveforms may be modulated with the sound signal associated with the third sound to generate the signal indicative of the one or more audio cues. The audio cues may enable a user to perceive the third sound coming from the given azimuth and elevation.

At 710, the signal indicative of the one or more audio cues is output by the one or more transducers of the earcup to facilitate spatial localization of third sound via the pinna. For instance, the signal indicative of the one or more audio cues may be input into the transducer of the earcup. The transducer may convert the signal to sound indicative of the one or more audio cues. The audio cues may facilitate spatialization of the sound associated with the sound signal.

In some examples the sound signal associated with the third sound may also be mixed with the signal indicative of the one or more audio cues. Then, the mixed signal may be input into the transducer for output as sound. The mixed signal may allow a user to hear the third sound as well as perceive the one or more audio cues so as to facilitate spatialization of the third sound. The signal indicative of the one or more audio cues may be mixed with the sound signal associated with the third sound in various proportions.

In some examples, the transducer may output sound associated with multiple signals where sound associated with each signal is spatialized. For instance, a first signal may be modulated with a first non-linear transfer function and a second signal may be modulated with a second transfer function to generate a signal indicative of audio cues for the first and second signal. Each non-linear transfer function may be determined in accordance with FIG. 7. The signal generated by modulating first signal and second signal may be input into the transducer. The transducer may output sound such that the sound associated with the first and second signal are each spatialized. Other variations are also possible.

FIG. 7 describes the functions for providing audio cues for a single pinna of an individual, e.g., a left pinna or a right pinna. Audio cues may need to be provided to the other pinna to facilitate spatial localization. To facilitate this, the non-linear transfer function for the other pinna associated with the single pinna, e.g., left pinna or right pinna, may need to be determined.

In one example, this determination may be made assuming the non-linear transfer function associated with the left and right pinna is similar. This assumption is based on the left and right pinnas being symmetrical. As a result, the same non-linear transfer function may be used to output the sound to each ear. The same non-linear transfer function may be used to generate the signal indicative of the one or more audio cues for each ear which is output to each ear in a manner similar to steps 708 and 710.

In another example, this determination may be made assuming that the non-linear transfer function associated with the left and right pinna is correlated. Based on this correlation, the non-linear transfer function for one pinna may be used to determine the non-linear transfer function for the other pinna. For instance, during the learning phase, the non-linear transfer function for the left and right pinna of an individual may be determined and associated together. The determined non-linear transfer function at 706 may be based on the non-linear transfer function of the left pinna of the individual determined during the learning phase. The non-linear transfer function of the right pinna may be the associated non-linear transfer function determined during the learning phase for the individual. Respective non-linear transfer functions may be used to generate the signal indicative of the one or more audio cues which is output to the ear in a manner similar to steps 708 and 710.

As yet another example, the non-linear transfer function may be determined biaurally, i.e., both pinnas characterized independently. For example, the earcup shown in FIG. 5 may be placed on one pinna and then moved to another pinna to determine respective the non-linear transfer functions for each pinna. As another example, a personal audio delivery device may have two earcups each with one or more transducers and microphones to facilitate determining the non-linear transfer function for each ear instead of having to move the earcup from one to the other pinna. In this case, a respective non-linear transfer function may be used to generate the signal indicative of the one or more audio cues which is output to the ear in a manner similar to steps 708 and 710.

A relationship may exist between an image of the pinna and the non-linear transfer function. In this regard, the image of the pinna may be used to determine the non-linear transfer function of the pinna rather than using a frequency response of the pinna a result of sound being directed toward the pinna and detected by a microphone.

Figure 11:
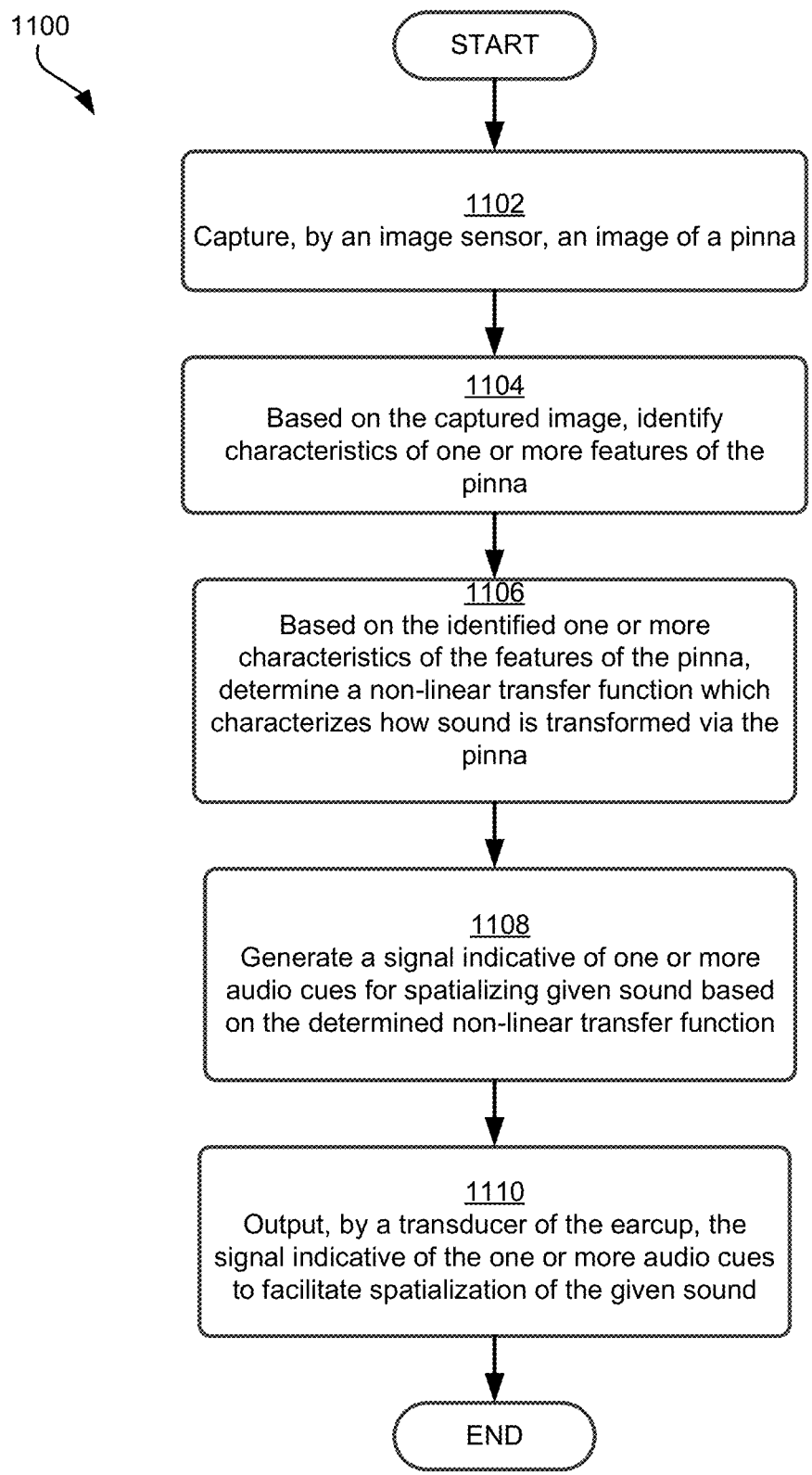
FIG. 11 is an example flow chart of functions associated with an image-based method for personalizing audio reproduction.

FIG. 11 shows a flow chart of functions 1100 associated with determining a transfer function of the pinna based on an image.

Briefly, at 1102, an image sensor in the earcup may capture an image of the pinna. At 1104, based on the image, characteristics of one or more features of the pinna is identified. At 1106, based on the identified characteristics of the one or more features, a non-linear transfer function is determined which characterizes how sound is received (e.g., transformed and/or modulated) at the pinna. At 1108, a signal indicative of one or more audio cues may be generated for given sound based on the determined non-linear transfer function. At 1110, the signal indicative of the one or more audio cues may be output by a transducer to facilitate the spatial localization of the given sound.

Figure 12:
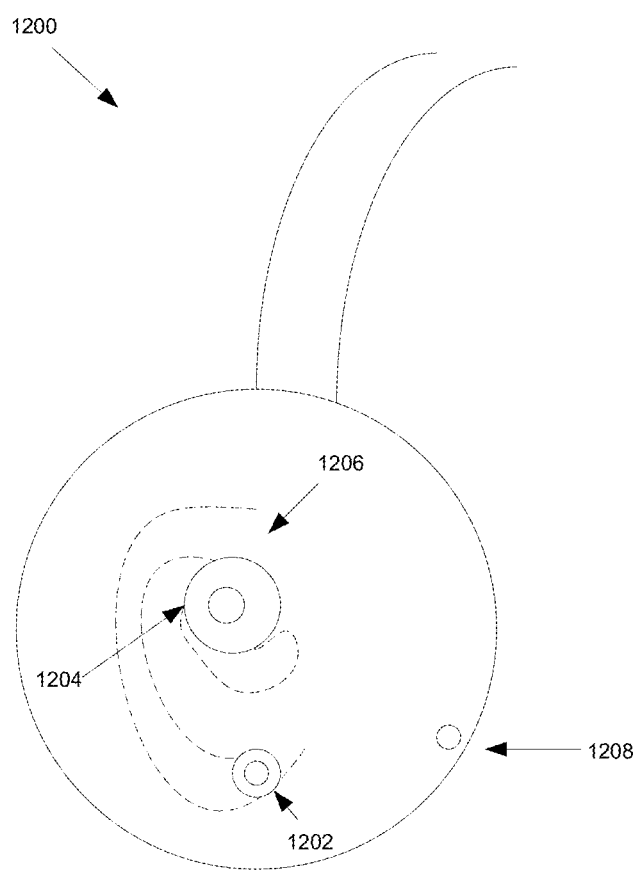
FIG. 12 shows an example earcup arranged to capture an image of a pinna.

FIG. 12 shows an example earcup 1200 arranged to capture an image of a pinna. The earcup 1200 may have one or more image sensors 1202. The image sensor 1202 may output an image of the pinna. The image sensor 1202 may be positioned around a transducer 1204 so as to obtain an unobstructed image of the pinna 1206.

The image may be captured in many ways based on an indication. In one example, the indication may take the form of a button press. The earcup may have a button (or some other input mechanism) which when pressed causes the image sensor to capture the image of the pinna. In this regard, the user may place the earcup in front of the pinna and press the button which causes the image sensor to capture the image of the pinna. In another example, the indication may be a movement of the earcup. The movement may cause a signal to be sent to the image sensor which in turn causes the image sensor to capture the image of the pinna and send the captured image to the processing engine.

The movement may be detected by a sensor 1208 such as a motion sensor and/or orientation sensor at the earcup 1200. For example, the motion sensor 1208 may be an accelerometer which measures acceleration of the earcup or a gyroscope which provides an indication of a change in orientation of the earcup. The motion sensor 1208 may be arranged to output a signal when the earcup is moved and not output a signal when the earcup is not moved. Other variations are also possible.

Figure 13:
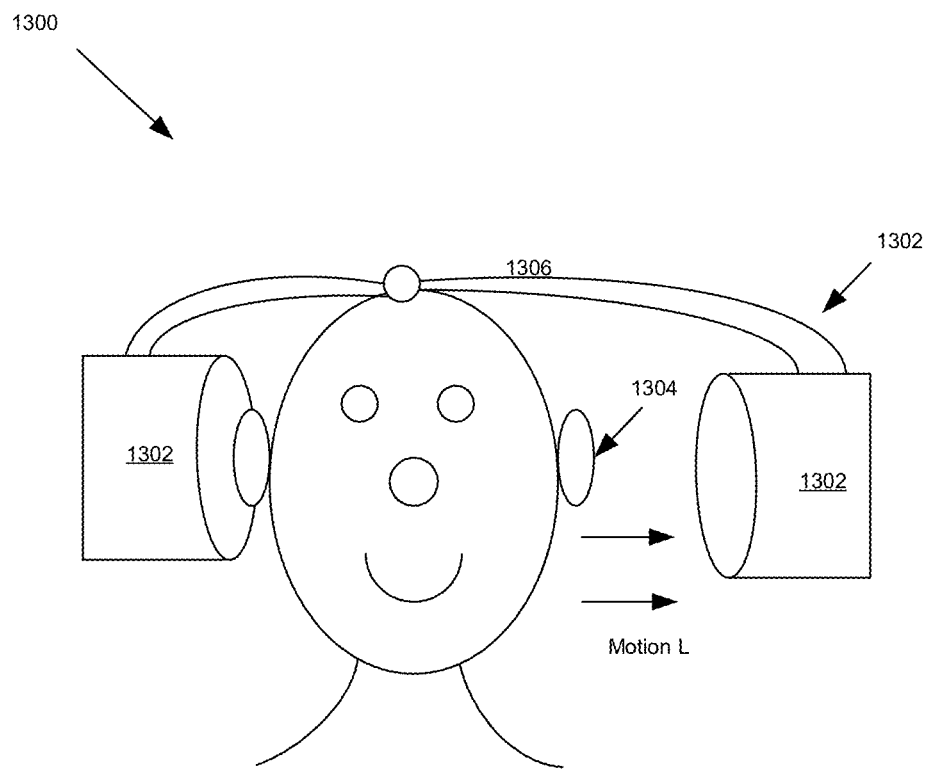
FIG. 13 shows an example of moving an earcup from the pinna to capture an image of the pinna.

FIG. 13 shows an example 1300 of moving an earcup 1302 from a pinna 1304 to cause the image of the pinna to be captured. Earcups 1302 may be normally seated on each pinna 1304. A headband 1306 may connect each earcup together. The headband 1306 may apply a tension to the earcup 1302 when placed on a head 1308 such that each earcup 1302 remains seated on the pinna 1304. The earcup 1302 may be moved from the pinna 1304 by pulling the earcup 1302 away from the pinna 1304. The earcup 1302 may be moved by applying a force to the earcup 1302 stronger than the tension which the headband 1306 applies to seat an earcup 1302 on a pinna 1304. As illustrated, the movement may be a natural linear motion L such that the other earcup which is not moved remains stable on the pinna 1304. The distance that the earcup 1302 can be pulled may range from one to three inches, depending on a tension on the headband 1306.

The motion sensor may send a signal to the image sensor based on detecting the movement of the earcup to capture the image of the pinna. In one example, the signal may be sent at a same time the movement is detected. In another example, the signal may be sent at a predefined time after the movement is detected. For example, a timer may be started when the signal indicative of movement is detected and the signal may be sent to the image sensor after a predefined time has passed. The predefined time may be sufficient enough for the earcup to be moved so that an air gap between the ear cup and the pinna allows ambient light to illuminate the pinna. The ambient light may improve an image quality of the captured image.

In yet another example, the signal may be sent when the earcup is a certain distance from the pinna. The earcup may have a proximity sensor to detect a proximity between two objects without physically touching either object. In some examples, the proximity sensor may be part of the motion sensor 1208 or a separate sensor. The proximity sensor may output a distance between the earcup and pinna. This distance may be monitored and when the distance is greater than or equal to the certain distance, the motion sensor may send the signal to the image sensor.

Characteristics of the image sensor may dictate the distance between the pinna and earcup when the proximity sensor sends the signal capture the image of the pinna. In one example, the distance may be based on an ability of the image sensor to capture detail of the pinna at that distance. In another example, the distance may be based on the image sensor being able to focus on the pinna. In yet another example, the distance may be based on the image sensor focal length and view angle. In another example, the distance may be sufficient for an air gap between the ear cup and the pinna to allow sufficient ambient light to illuminate the pinna. The ambient light may improve an image quality of the captured image.

As described, the image sensor may receive the signal to capture the image of the pinna and responsively capture the image. The image sensor may provide the image to the processing engine.

At 1104, characteristics of one or more features of the pinna is determined from the image. Various image processing techniques may be used by the processing engine to determine the characteristics of the features of the pinna, including identifying a feature of the pinna, extracting the feature from the image, and then determining a characteristic of the feature. The characteristics may include, but not be limited to an overall size and shape of the pinna (e.g., length, width, radius), a size and shape (e.g., length, width, radius) of the helix, fossa, cymba conchae, cavum conche, tragus, ear notch, antihelix, and/or antitragus among other features, and a relative distance between two or more of the helix, fossa, cymba conchae, cavum conche, tragus, ear notch, antihelix among other features.

At step 1106, based on the identified characteristics of the one or more features, a non-linear transfer function is determined which characterizes how the first sound is transformed via the pinna. The non-linear transfer function may be determined in a manner similar to the process described with respect to FIGS. 10A-C.

A direct measurement may be performed during a learning process for each of a plurality of individuals different from the individual for whom the image of the pinna is captured at step 1102. The direct measurement for each of the plurality of individuals may result in determining a plurality of non-linear transfer functions. Each non-linear transfer function may be associated with a sensor output such as an image of the pinna.

Figure 14A:
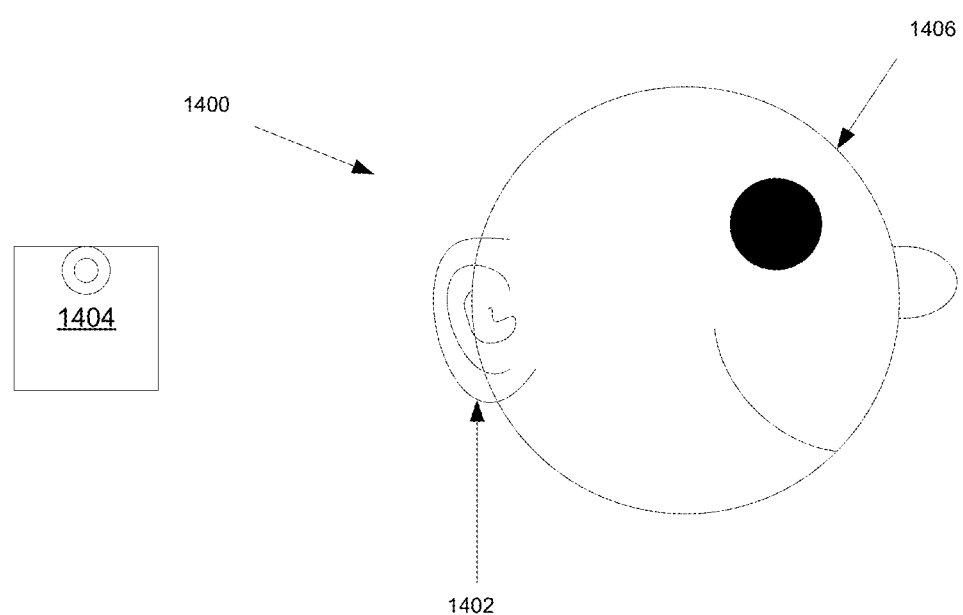
FIGS. 14A-B illustrate example arrangements associated with determining a non-linear transfer function.

FIG. 14A illustrates an example arrangement 1400 for determining the sensor output. The sensor output may take the form of an image of the pinna 1402 captured by an image sensor 1404 for an individual 1406. The non-linear transfer function may be associated with the image of the pinna.

Figure 14B:
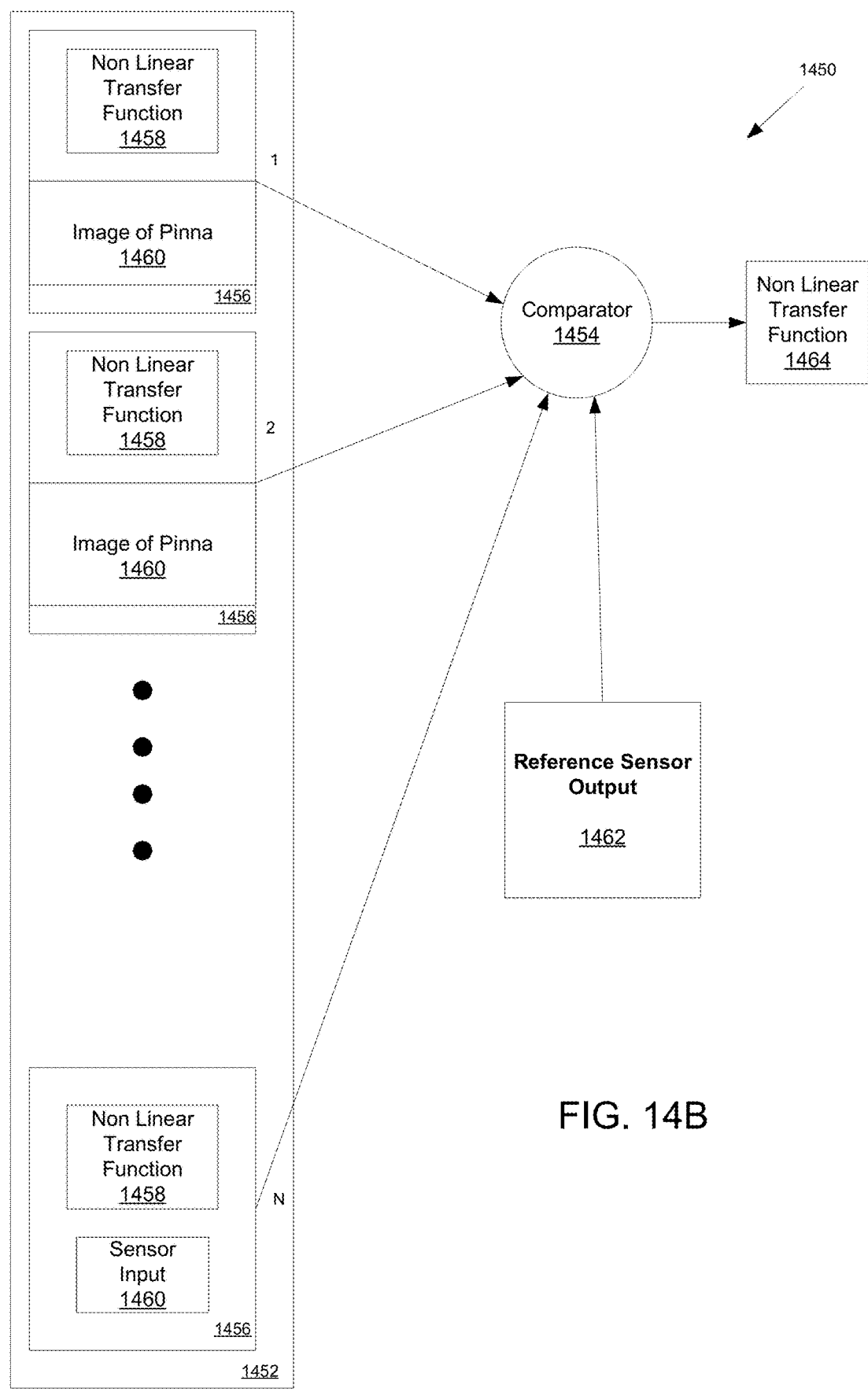

FIG. 14B illustrates an example arrangement 1450 for determining the non-linear transfer function at step 1106 without having to perform a direct measurement for the individual. The non-linear transfer function may be based on the plurality of non-linear transfer functions and associated images of pinnas determined during the learning process.

The example arrangement 1450 may include a database 1452 and comparator 1454. The database 1452 and comparator 1454 may reside on the personal audio delivery device, server, or some other device. The database 1452 may store the plurality of non-linear transfer functions and associated images of pinnas determined during the learning process. An entry 1456 in the database 1454 may define a respective non-linear transfer function 1458 and associated image of pinna 1460 of the plurality of non-linear transfer functions and associated images of pinnas determined during the learning process. The database may have a plurality of entries 1:N.

The comparator 1460 may be arranged to compare each image of pinna 1460 associated with a respective non-linear transfer function 1458 to a reference sensor output 1462 to identify a sensor output 1460 in the entries 1:N which is closest to the reference sensor output 1462. The reference sensor output 1462 may be the image of pinna captured at step 1102. Further, the image of pinna 1460 may be an image of a pinna determined in a manner similar to how the reference sensor output 1462 is determined.

The comparison performed by the comparator 1454 may be based on comparing characteristics of the features of the pinna associated with the reference sensor output 1462 with corresponding characteristics of one or more features of the pinna associated with the image of the pinna 1460. The comparator 1454 may output a non-linear transfer function 1464. The non-linear transfer function 1464 may be a non-linear transfer function 1458 associated with the image of the pinna 1460 which is close to (e.g., most closely matches) the reference sensor output 1462. The closeness of match may be based on a distance between characteristics of the features of the pinna associated with the reference sensor output 1462 and corresponding characteristics of one or more features of the pinna associated with the image of the pinna 1460, among other measures.

In this regard, the direct measurement may not need to be performed on the pinna of the individual to determine the non-linear transfer function at step 1106. Instead, the non-linear transfer function may be based on the plurality of non-linear transfer functions determined during the learning process and stored and the database 1452 and used in real time to determine the non-linear transfer function 1464.

In another example, the non-linear transfer function at step 1106 may be determined based on a combination of one or more of the plurality of non-linear transfer functions stored in the database 1452. For instance, one or more of the plurality of non-linear transfer functions may be weighed to determine non-linear transfer function at step 1106. The weighting may be based on a closeness of match between the image of the pinna captured at 1102 and the image of the pinna associated with a non-linear transfer function of the plurality of non-linear transfer functions. For example, characteristics of one or more features of the pinna in the captured image at step 1102 may be compared to corresponding characteristics of one or more features of the pinna in an image of the pinna associated with a non-linear transfer function of the plurality of non-linear transfer functions. A closer match may result in a stronger weighting while a farther match may result in a weaker weighting. Then, the weighed non-linear transfer functions may be combined to form the determined non-linear transfer function at step 1106.

In yet another example, the non-linear transfer function at step 1106 may be based on a function similar to that shown in FIG. 10C. The plurality of non-linear transfer functions and associated images of the pinna may be parameterized via numerical analysis methods to define a function such that an input to the function may be the image of the pinna captured at step 1102 and an output of the function may be the determined non-linear transfer function for the image of the pinna captured at step 1102. The functions may take a variety of forms.

For instance, the function may take the form of a model fit to each of the non-linear transfer functions associated with the image of the pinna determined during the learning phase using well known data fitting techniques such as neural networks. The image of the pinna captured at step 1102 may be input into the model and the model may output the non-linear transfer function for the image of the pinna captured at step 1102.

In some examples, the non-linear transfer function associated with step 1106 may be stored, e.g., in memory. In this regard, a process for determining the non-linear transfer function may be personalized to a user and need to be determined one-time and used as described below.

At 1108, a signal indicative of one or more audio cues may be generated for given sound based on the determined non-linear transfer function. The one or more audio cues may be generated in a manner similar to that described with respect to step 708 of FIG. 7.

At 1110, the signal indicative of the one or more audio cues may be output to facilitate the spatial localization of the given sound via the pinna. The one or more audio cues may be output by a transducer in a manner similar to that described with respect to step 710 of FIG. 7.

One or more audio cues may be output to a pinna based the functions of FIG. 11. An individual may have two pinnas. The non-linear transfer function for the other pinna may be also determined. The non-linear transfer function may be determined biaurally, i.e., both pinnas are characterized independently. Alternatively, it may be assumed that both pinnas are similar and the transfer function of one pinna may be the same as the other pinna. Still alternatively, it may be assumed that both pinnas are similar and the non-linear transfer function of one pinna may be correlated to the transfer function of the other pinna.

In some examples, the earcup when capturing the image of the pinna may not only be linearly moved but could also be rotated in a plurality of dimensions. The motion sensor may detect this rotation and provide it to the processing engine. Then the processing engine may apply a rotation matrix to rotate the captured image to be parallel with a given plane to facilitate comparison with the images of the pinna associated with the plurality of non-linear features determined during the learning process also parallel with the given plane. Additionally, or alternatively, the images of the pinna associated with the plurality of non-linear features determined during the learning process may be rotated to facilitate the comparison.

The non-linear transfer function may be determined using either the earcup with one or more microphones and or the earcup which has an image sensor. However, the non-linear transfer function may be also determined using a headphone having one earcup with one or more microphones and another earcup which has one or more image sensors. The process may involve combining the functions of FIGS. 7 and 11.

Figure 15:
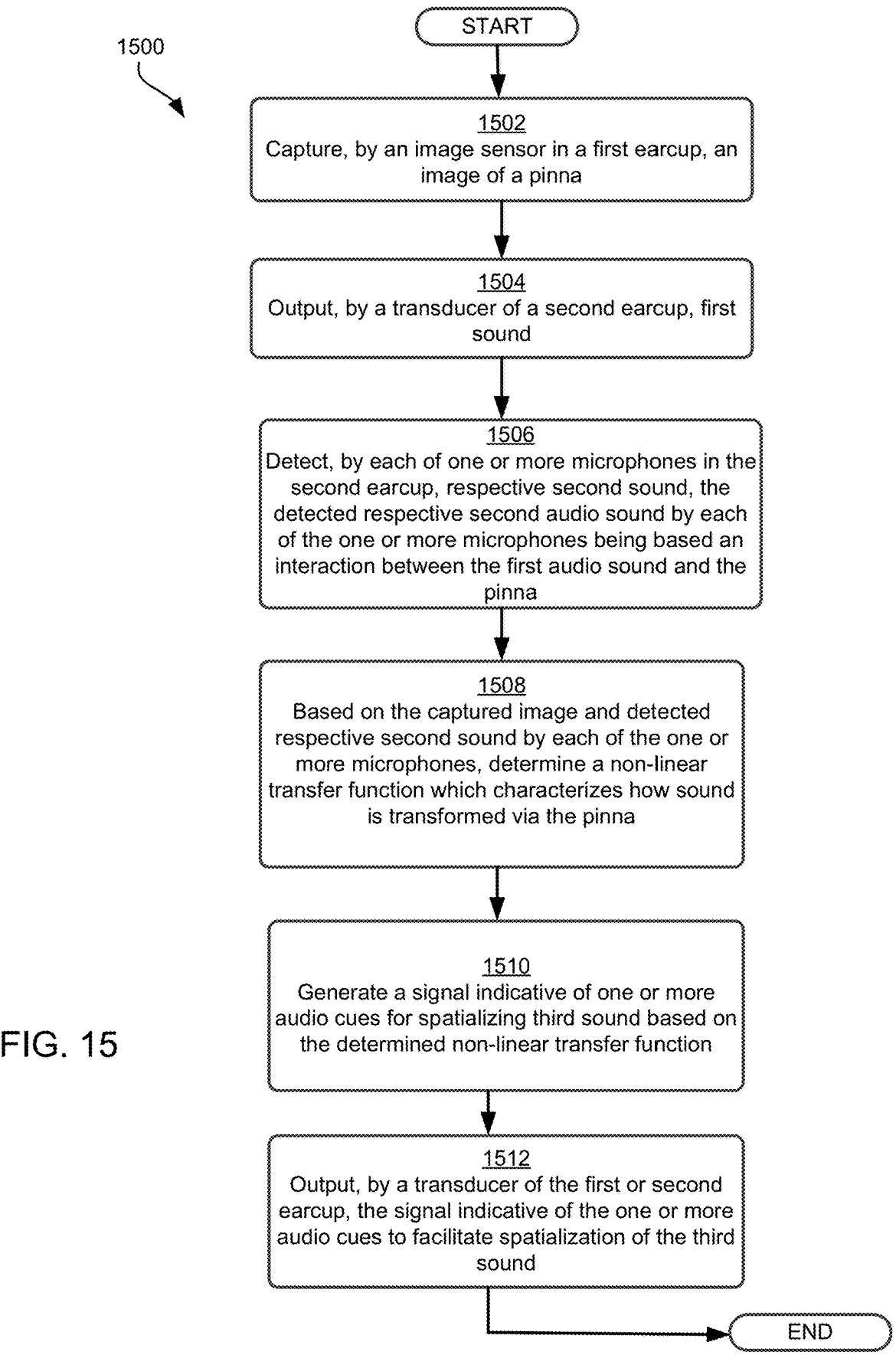
FIG. 15 is a flow chart of functions associated with a sound-based and image-based method for personalizing audio reproduction.

FIG. 15 is a flow chart 1500 of functions associated with this combination. Briefly, at 1502, an image of a pinna is captured by a first earcup. At 1504, first sound is output by a transducer of the second earcup. At 1506, respective second sound is detected by each of the one or more microphones in the second earcup. The respective second sound for a microphone may be detected based on an interaction between the first sound and the pinna on which the earcup is worn at the location of the microphone. At 1508, based on the captured image and the detected respective second sound by each of the one or more microphones, a non-linear transfer function is determined which characterizes how sound is transformed via the pinna. At 1510, a signal indicative of one or more audio cues may be generated for spatializing third sound based on the determined non-linear transfer function. At 1512, the signal indicative of the one or more audio cues is output by a transducer of the first or second earcup to facilitate spatialization of the third sound.

Referring back, at 1502, an image of a pinna is captured. The image may be captured using an image sensor in one of the earcups of the headphone in a manner similar to that described at step 1102 of FIG. 11. In some examples, the image may be captured when the earcup of the headphone is moved from the pinna. In some examples, the earcup may have a motion sensor and proximity sensor to determine movement of the earcup and a distance between the earcup and pinna respectively. The captured image may be sent to the processing engine.

At 1504, first sound is output by a second earcup. The processing engine may cause the first sound to be output by a transducer in the second earcup. The first sound may be played while the image is being captured, before the image is captured, or after the image is captured. The first sound may take a variety of forms including a chirp, impulse, or bandlimited sound.

At 1506, respective second sound is detected by each of the one or more microphones in the earcup based on the output of the first audio sound. The one or more microphones in the earcup may each detect respective second sound based on an interaction between the first sound and the pinna at the location of the microphone. The respective detected second sound for each microphone may be audio scatter. The first sound is reflected, resonated, and/or modulated by the pinna and this audio scatter is detected by a microphone in the earcup as the respective second sound. The first sound may be in an audible range. As a result, the start of the first sound output may indicate to a user that a determination of the non-linear transfer function has begun and an end of the first sound output may indicate the determination of the non-linear transfer function is almost complete. In this way, the first sound may also provide user feedback on the progress associated with determining the non-linear transfer function.

The detected respective second sound by each of the one or more microphones may be sent to the processing engine. At 1508, based on the captured image and the detected respective second sound by each of the one or more microphones, a non-linear transfer function may be determined which characterizes how the pinna transforms sound. The non-linear transfer function may be determined by the processing engine. The non-linear transfer function may be determined in a variety of ways.

A direct measurement similar to that shown in FIG. 10A may be performed during a learning process for each individual of a plurality of individuals different from whom the image is captured at step 1502 and second sound is detected at step 1506 to determine non-linear transfer functions. Additionally, an image of a pinna may be determined for each individual and associated with the non-linear transfer function for each individual. The image of the pinna may be captured in a manner similar to FIG. 14A and how the image of the pinna is captured at step 1502. In this regard, the learning process may involve determining a plurality of non-linear transfer functions and associated images of pinna.

Figure 16:
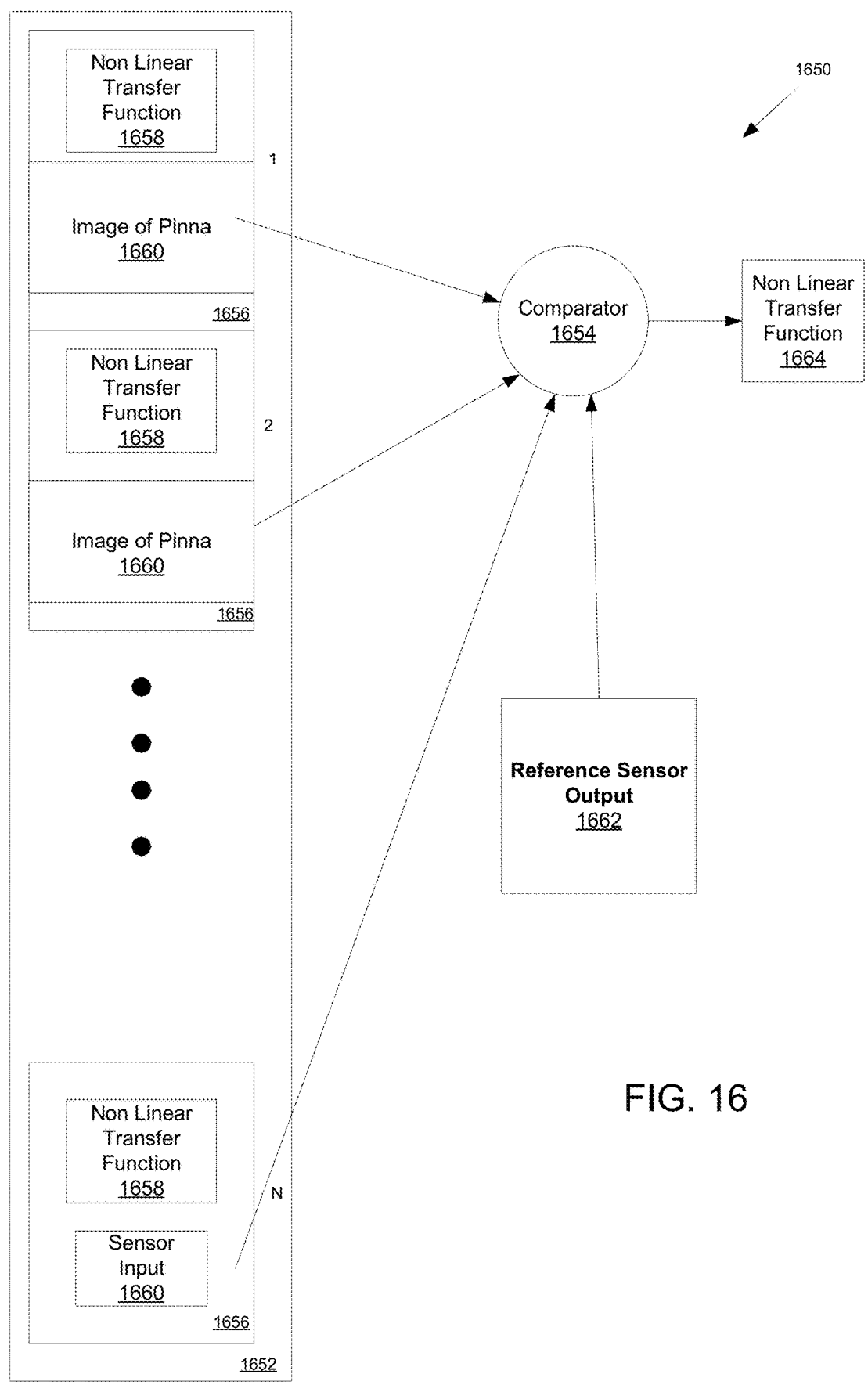
FIG. 16 illustrates an example arrangement associated with determining a non-linear transfer function.

FIG. 16 illustrates an example arrangement 1650 for determining the non-linear transfer function at step 1508. The non-linear transfer function at step 1508 may be based on the plurality of non-linear transfer functions and images of the pinna determined during the learning process.

The example arrangement 1650 may include a database 1652 and comparator 1654. The database 1652 and comparator 1654 may reside on the personal audio delivery device, server, or some other device. The database 1652 may store the plurality of non-linear transfer functions and associated images of the pinna determined during the learning process. An entry 1656 in the database 1652 may define a respective non-linear transfer function 1658 and associated image of a pinna 1660 of the plurality of non-linear transfer functions determined during the learning process. The database may have a plurality of entries 1:N.

A reference sensor output 1662 may be a sensor output for the individual for whom the audio cues is to be generated, e.g., detected respective second sound by the one or more microphones associated with step 1506 and an image of pinna associated with step 1502. The comparator 1654 may be arranged to compare the image of the pinna 1660 associated with a respective non-linear transfer function 1658 to an image of the pinna associated with reference sensor output 1662. This comparison may be assigned a first correlation score. Additionally, the comparator 1654 may be arranged to compare frequency responses of a respective non-linear transfer function 1658 to the detected respective second sound by each of the one or more microphones associated with reference sensor output 1662. This comparison may be assigned a second correlation score.

The respective correlation scores for a same non-linear transfer function may be combined, e.g., summed, to form a combined score. The comparator 1654 may output a non-linear transfer function 1658 of the plurality of non-linear transfer functions which has a highest combined score as the non-linear transfer function 1664 associated with step 1508. In this regard, a non-linear transfer function associated with an image of the pinna which is correlated to the image of the pinna captured at 1502 and frequency responses of the non-linear transfer function which is correlated to the detected respective second sound by the one or more microphones at step 1506 may be the determined non-linear transfer function at step 1508.

In another example, the determined non-linear transfer function at step 1508 may be based on a combination of one or more of the plurality of non-linear transfer functions. For instance, one or more of the plurality of non-linear transfer functions may be weighed to determine non-linear transfer function at step 1508. The weighting of a non-linear transfer function of the plurality of non-linear transfer functions may be based on a first and second correlation score associated with the non-linear transfer function of the plurality of non-linear transfer functions. For instance, higher correlation scores may result in a stronger weighting while lower correlation scores may result in a weaker weighting. Then, the weighed non-linear transfer functions may be combined to form the determined non-linear transfer function at step 1508.

In yet another example, the non-linear transfer function at step 1508 may be based on a function similar to that shown in FIG. 9C. Each non-linear transfer function of the plurality of non-linear transfer functions and a respective image of a pinna may be parameterized via numerical analysis methods to define a function such that an input to the function may be the detected respective second sound of the one or more microphones at step 1506 and the image of the pinna captured at 1502 and an output of the function may be the determined non-linear transfer function. The functions may take a variety of forms.

For instance, the function may take the form of a model fit to each of the non-linear transfer functions and image of the pinna determined during the learning phase using well known data fitting techniques such as neural networks. The detected respective second sound by the one or more microphones at 1506 and the image of the pinna captured at 1502 may be input into the model and the model may output the non-linear transfer function.

In some examples, the non-linear transfer function associated with step 1506 may be stored, e.g., in memory. In this regard, a process for determining the non-linear transfer function may be personalized to a user and need to be determined one-time and used as described below.

At 1510, a signal indicative of one or more audio cues may be generated for spatializing third sound based on the determined non-linear transfer function. The one or more audio cues may be output in a manner similar to that described with respect to step 708 of FIG. 7.

At 1512, the signal indicative of the one or more audio cues may be output to facilitate the spatial localization of the third sound via the pinna. The one or more audio cues may be output by a transducer of the first or second earcup in a manner similar to that described with respect to step 710 of FIG. 7.

A non-linear transfer function for a single pinna of an individual is determined based the functions of FIG. 15. The non-linear transfer function for the other pinna may be also determined. The non-linear transfer function may be determined biaurally, i.e., both pinnas are characterized independently. Alternatively, it may be assumed that both pinnas are similar and the transfer function of one pinna may be the same as the other pinna.

In the example described above, a headphone may have one earcup with an image sensor, motion sensor and/or proximity sensor and another earcup with a transducer and microphone. Each earcup is used to determine the non-linear transfer function. However, a single earcup might be arranged with both the image sensor, transducer, microphone, motion sensor and/or proximity sensor for determining the non-linear transfer function.

In some examples, a mobile device such as a phone, tablet, handheld computing device, watch, etc. instead of an earcup with an image sensor may be used to determine the non-linear transfer function which characterizes how the pinna transforms sound.

Figure 17:
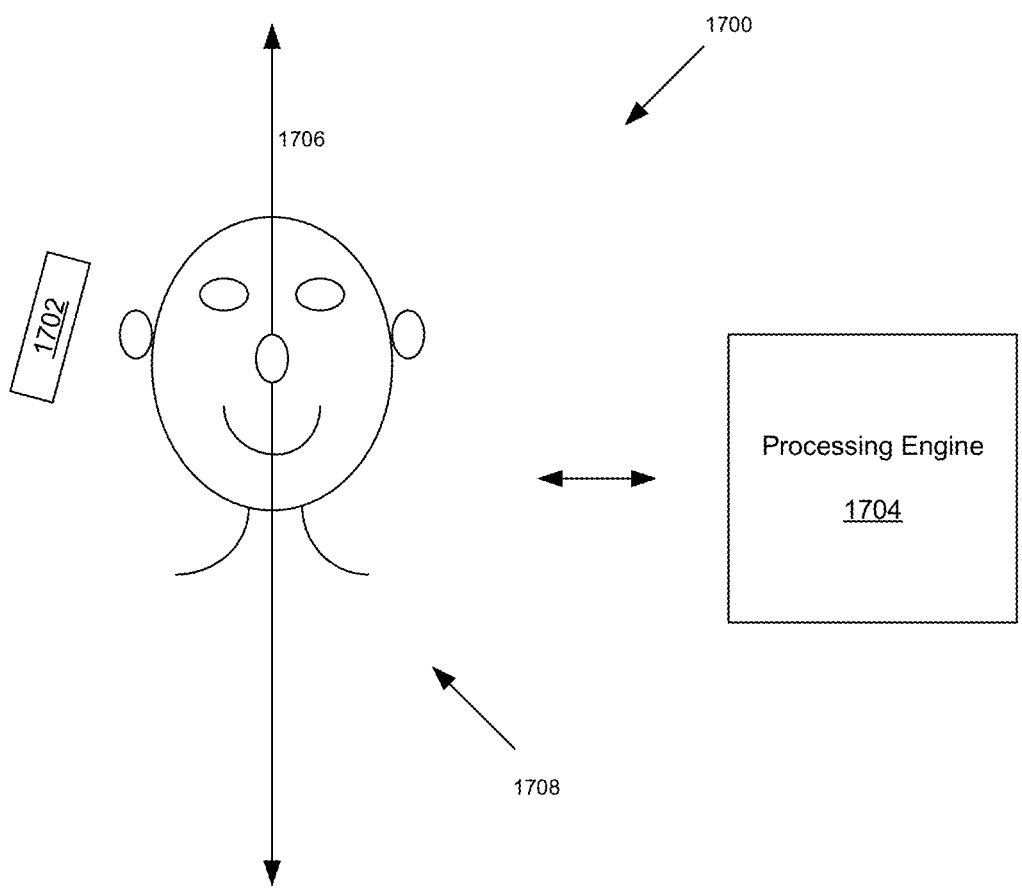
FIG. 17 shows another system for personalizing audio reproduction.

FIG. 17 shows another system 1700 for personalizing audio reproduction. The system 1700 may include the mobile device 1702 and a processing engine 1704. The mobile device 1702 may have a plurality of sensors. The sensors may include an image sensor, motion sensor, and/or proximity sensor, among others. The mobile device may be oriented with respect to a user's median plane 1706 of a user 1708 of the mobile device. The user's median plane 1706 is the plane slicing the user's head in 2 halfs, i.e., left and right.

The processing engine 1704 may process the signals associated with the plurality of sensors. The processing engine 1704 may determine the non-linear transfer function. In some examples, the processing engine 1704 may be a processor local to the mobile device 1702. The processor may be a central processing unit (CPU) which executes computer instructions stored in storage such as memory. The processor may process the signals associated with the plurality of sensors. In other examples, the processing engine 1704 may be remote to the mobile device 1702. For example, the processing engine 1704 may be a server accessible by the mobile device via a wired or wireless network. The server may process the signals associated with the plurality of sensors. The mobile device 1702 may have circuitry for communicating with the server to facilitate processing of the signals associated with the plurality of sensors. Similar issues with respect to latency and battery consumption may exist with a local processor at the mobile device versus a remote server as described with respect to the system in FIGS. 6A and 6B. In some cases, the processing engine 1704 may include the local processor and remote sever.

Figure 18:
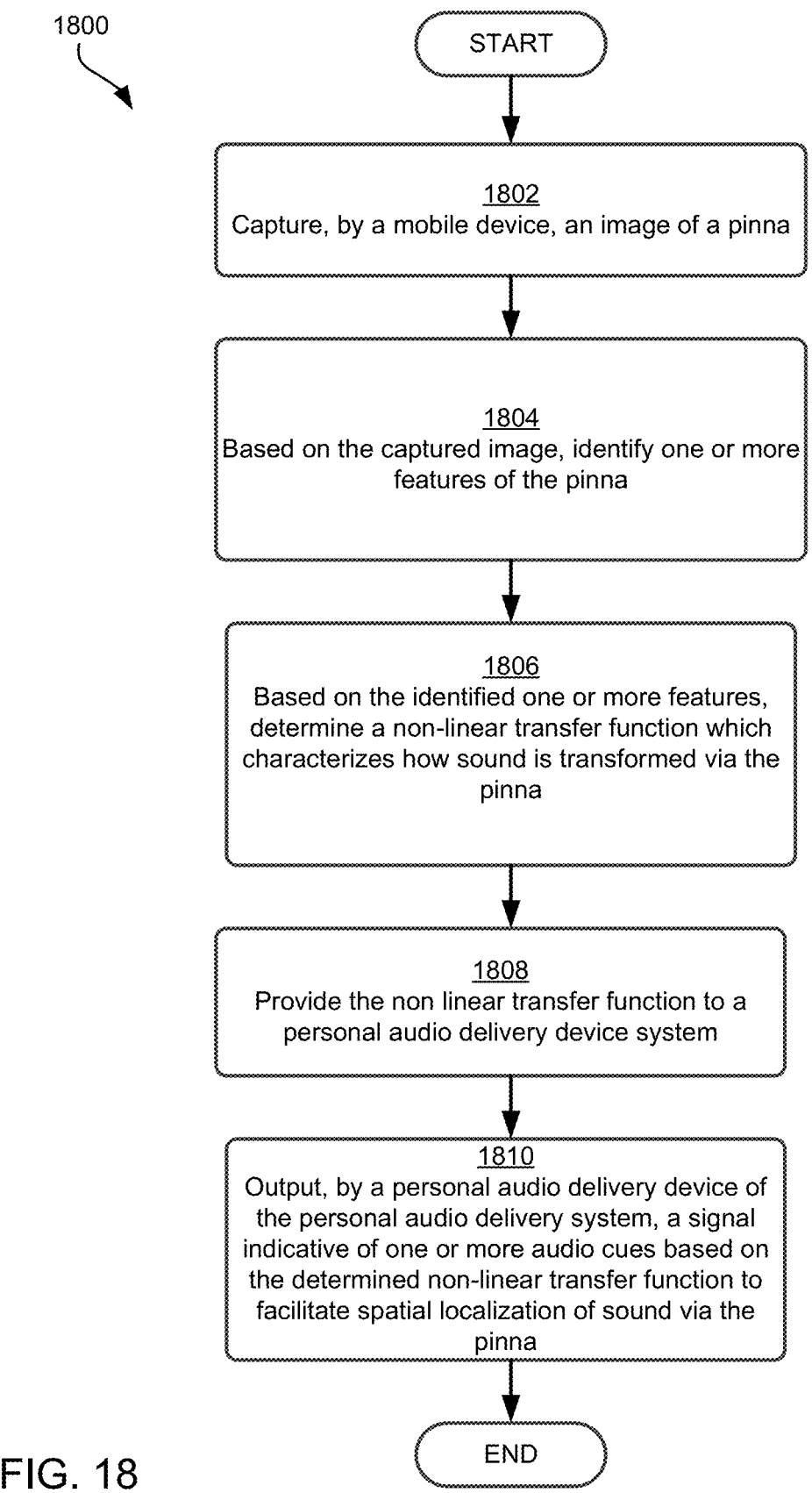
FIG. 18 shows an example flow chart of functions associated with an image-based method for personalizing audio reproduction.

FIG. 18 shows a flow chart of functions 1800 associated with determining a non-linear transfer function of a pinna using the mobile device.

Briefly, at 1802, an image of the pinna may be captured by a mobile device. At 1804, characteristics of one or more features of the pinna is identified based on the captured image. At 1806, based on the identified characteristics, a non-linear transfer function is determined which characterizes how sound is received (e.g., transformed and/or modulated) at the pinna. At 1808, the non-linear transfer function is provided to a personal audio delivery system. At 1810, a signal indicative of one or more audio cues may be output based on the determined non-linear transfer function to facilitate the spatial localization of sound via the pinna.

Referring back, at 1802, an image of the pinna may be captured by the mobile device. A user may hold the mobile device towards his/her ear such that the image sensor of the mobile device is facing the pinna. The mobile device may automatically capture the image via the image sensor when the mobile device is at a certain distance from the pinna as indicated by the proximity sensor. Alternatively, the user may press a button on the mobile device to capture the image when the mobile device is held at a certain distance from the pinna. The captured image may be sent to the processing engine.

Additionally, or alternatively, the mobile device may be oriented at a certain angle with respect to the pinna. The orientation may be a rotation (in one or more directions) of the mobile device with respect to the user's median plane. The sensors, e.g., motion and/or orientation sensors, may detect this orientation of the mobile device when the image is captured and provide the orientation to the processing engine.

At 1804, characteristics of one or more features of the pinna is identified based on the captured image. Various image processing methods may be used to identify the characteristics of the one or more features. In some examples, the processing system may also apply a rotation matrix to rotate the image based on the orientation detected when the image was captured prior to identifying the characteristics of the features.

At 1806, based on the identified characteristics, a non-linear transfer function is determined which characterizes how sound is received (e.g., transformed and/or modulated) at the pinna. Details on this process are described with respect to step 1106 of FIG. 11. Characteristics of the one or more features of the pinna in the image captured at 1802 may be compared to characteristics of the one or more features of pinnas associated with the images of the pinnas associated with the non-linear transfer functions determined during a learning process. A non-linear transfer function associated with a closest match may be the determined non-linear transfer function as described above in a manner similar to FIGS. 14B and 10C.

At 1808, the non-linear transfer function is provided to a personal audio delivery system. The personal audio delivery system may be the system shown in FIGS. 6A and 6B having a personal audio delivery device or some other system. The mobile device may have a transducer for outputting sound. In some examples, the personal audio delivery system may be the same system as shown in FIG. 17 in which case step 1808 need not be performed since the system of FIG. 17 already has the non-linear transfer function.

At 1810, a signal indicative of one or more audio cues may be output based on the determined non-linear transfer function to facilitate the spatial localization of sound via the pinna. The one or more audio cues may be generated in a manner similar to that described with respect to step 708 of FIG. 7 and output in a manner similar to that described with respect to step 710 of FIG. 7.

Figure 19:
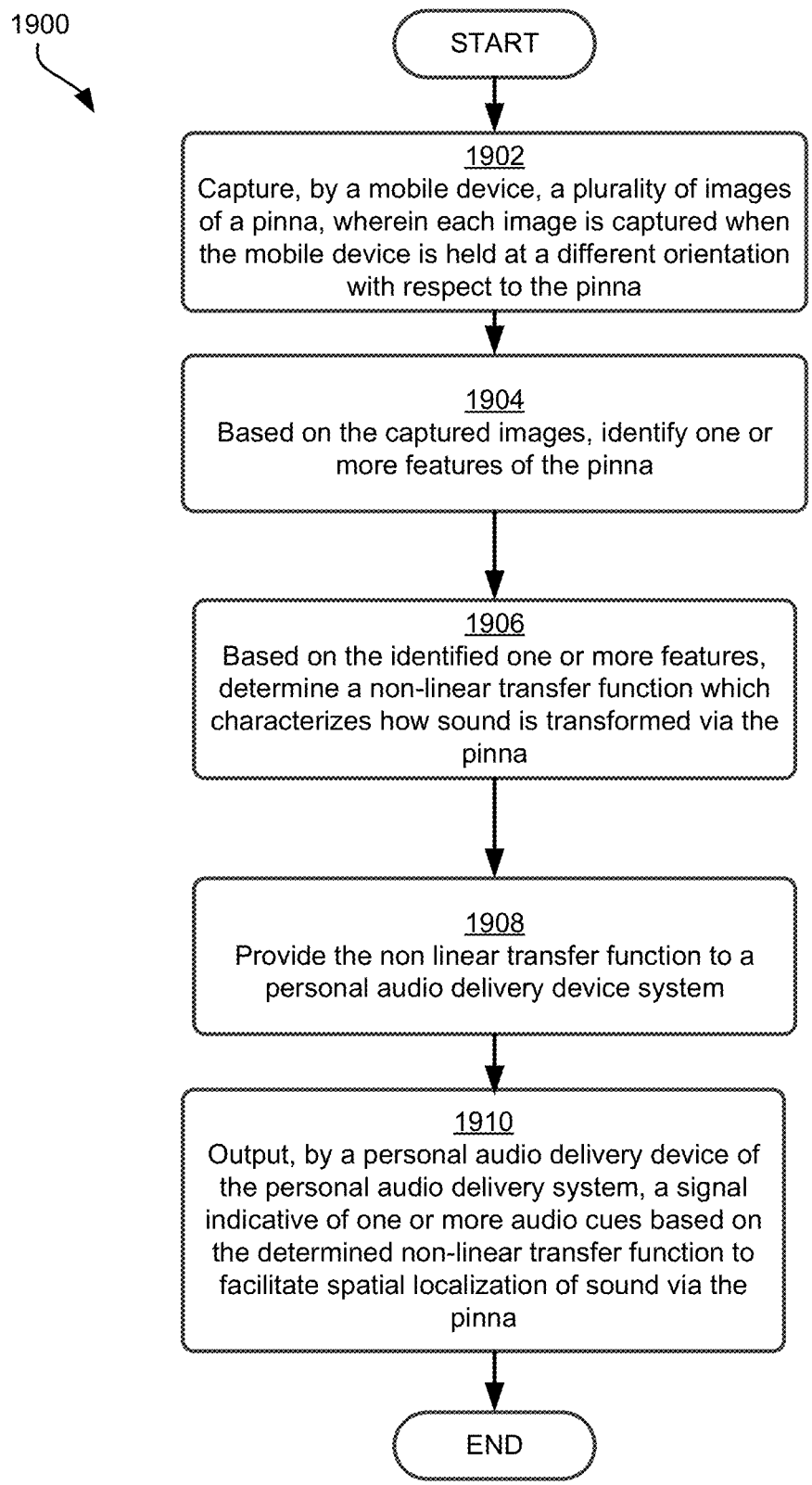
FIG. 19 shows another example flow chart of functions associated with an image-based method for personalizing audio reproduction.

FIG. 19 is another flow chart of functions 1900 associated with determining a non-linear transfer function of a pinna using a mobile device. In this flow chart, multi-dimensional features of the pinna may be accounted for in the determination of the non-linear transfer function.

Briefly, at 1902, a plurality of images of the pinna may be captured by a mobile device. Each image may be captured when the mobile device is orientated in a certain way with respect to the pinna. At 1904, characteristics of one or more features of the pinna is identified based on the captured images. At 1906, based on the identified characteristics, a non-linear transfer function is determined which characterizes how sound is transformed at the pinna. At 1908, the non-linear transfer function is provided to a personal audio delivery system. At 1910, one or more audio cues may be output based on the determined non-linear transfer function to facilitate the spatial localization of sound via the pinna.

Referring back, at 1902, a plurality of images of the pinna may be captured by a mobile device. The plurality of images may be images of the pinna at different orientations. Each image may be captured when the mobile device is orientated in a certain way with respect to a median plane.

Figure 20A:
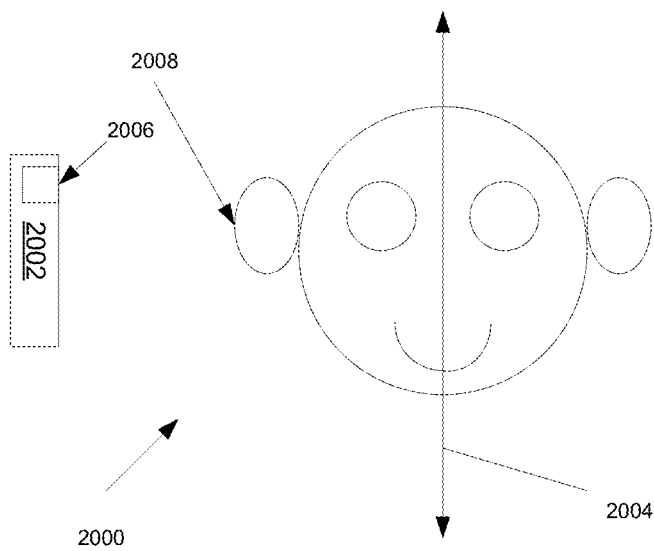
FIGS. 20A to 20C show example orientations of a mobile device with respect to a pinna.
Figure 20B:
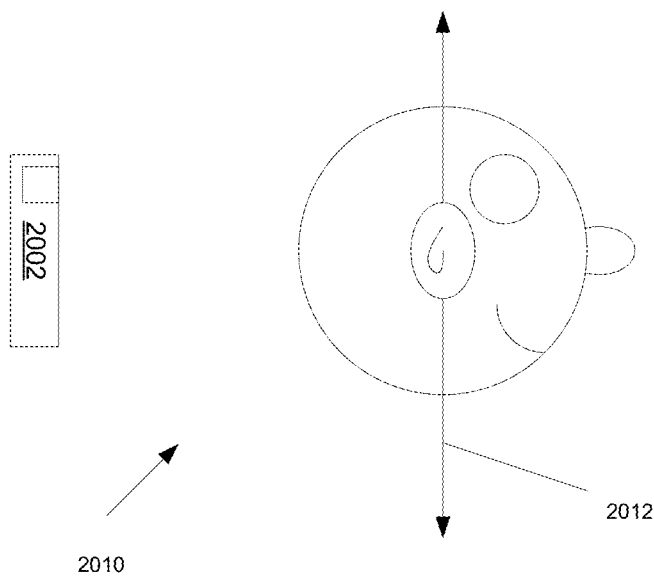
Figure 20C:
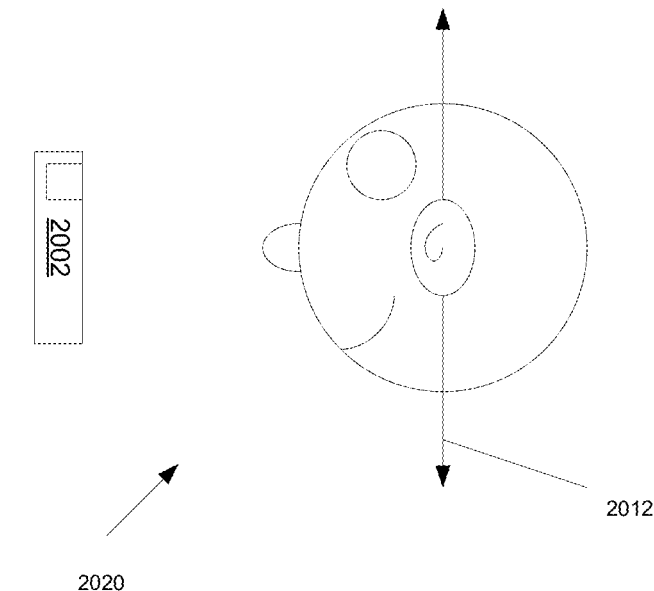

FIGS. 20A-C illustrates some examples orientations of the mobile device. The mobile device may be oriented with respect to the median plane to capture an image of the pinna.

FIG. 20A shows an example orientation 2000 where a mobile device 2002 is oriented parallel to a user's median plane 2004. The user's median plane 2004 may divide a head of a person symmetrically between the ears. An image sensor 2006 of the mobile device 2002 captures an image of a front of the pinna 2008.

FIG. 20B shows an example orientation 2010 where the mobile device 2002 is oriented parallel to a plane 2012 to capture the image of the pinna. The plane 2012 is the plane which passes through user's left and right ears and divides user's head in two halfs, i.e. front and back. The mobile device may be oriented parallel to a back half of the plane 2012. The image sensor of the mobile device captures an image of a back profile of the pinna 2008.

FIG. 20C shows an example orientation 2020 where the mobile 2002 device is oriented in parallel to a front half of the plane 2012 to capture the image of the pinna. The mobile device may be oriented parallel to a front half of the plane 2012. The image sensor of the mobile device captures an image of a front profile of the pinna 2008.

The mobile device may be held by a user and moved to capture images of the pinna at different orientations. Instead of moving the mobile device to the different orientations, a user may hold the mobile device stationary and turn the head to capture the pinna at the different orientations. Alternatively, both the mobile device may be moved and the head turned to capture the image of the pinna at the different orientations.

The captured image at each orientation may be sent to the processing engine. At 1904, characteristics of one or more features of the pinna is identified based on the captured images. As an example, the images captured in multiple orientations may be post-processed, e.g., to remove noise, and/or combined to form a multi-dimensional image of the features of the pinna, e.g., a three-dimensional image. The multi-dimensional image may then be analyzed to identify the characteristics of the features of the pinna. As another example, each image may be separately analyzed to identify the characteristics of the features of the pinna, including a depth of the features based on the captured images. The captured image may be processed in other ways as well.

At 1906, based on the identified characteristics, a non-linear transfer function is determined which characterizes how sound is transformed by the pinna. Each of the plurality of non-linear transfer functions determined during a learning process may be associated with a respective plurality of images of the pinna. The respective plurality of images may be captured in a manner similar to how images of the pinna are captured at step 1902. The non-linear transfer may be based on comparing features of the pinna as indicated by the captured images at step 1902 and a respective plurality of images of the pinna associated with a non-linear transfer function of the plurality of non-linear transfer functions determined during the learning process. Details are generally described with respect to FIG. 14B and step 1106 of FIG. 11, the difference being that the image of the pinna 1456 takes the form of a respective plurality of images. The non-linear transfer function of the plurality of non-linear transfer functions having a respective plurality of images of the pinna with a close correlation to the plurality of images of the pinna captured at 1902 may be the determined non-linear transfer function at step 1906.

The non-linear transfer function may be determined in other ways. The other ways may include being based on a combination of the plurality of non-linear transfer functions determined during the learning process. Alternatively, the non-linear transfer function may be based on a function which takes as input the plurality of images captured at 1802 and which outputs the determined non-linear transfer function. The function may be a model trained on the plurality of non-linear transfer functions and associated plurality of images captured at different orientations.

At 1908, the non-linear transfer function is provided to a personal audio delivery system. The personal audio delivery system may be the system shown in FIG. 5 having a personal audio delivery device or some other system. In some examples, the personal audio delivery system may be the same system as shown in FIG. 17 in which case this step may not be performed since the system of FIG. 17 already determined the non-linear transfer function.

At 1910, a signal indicative of one or more audio cues may be output based on the determined non-linear transfer function to facilitate the spatial localization of sound via the pinna. The one or more audio cues may be generated in a manner similar to that described with respect to step 708 of FIG. 7 and output in a manner similar to that described with respect to step 710 of FIG. 7.

The mobile device is described above to capture one or more images of the pinna at the different orientations to determine the non-linear transfer function. However, instead of capturing images, the mobile device may capture the one or more images in the form of a sequence of images, e.g., video, rather that discrete images at the different orientations. For instance, mobile device may capture a video of the user moving the mobile device to the different orientations and/or the head turning to capture the pinna from different angles. Then, characteristics of the one or more features of the pinna to determine a non-linear transfer function for the pinna may be extracted using image processing techniques from the video and used to determine the non-linear transfer function for the pinna. Other variations are also possible.

The description above discloses, among other things, various example systems, methods, apparatus, and articles of manufacture including, among other components, firmware and/or software executed on hardware. It is understood that such examples are merely illustrative and should not be considered as limiting. For example, it is contemplated that any or all of the firmware, hardware, and/or software aspects or components can be embodied exclusively in hardware, exclusively in software, exclusively in firmware, or in any combination of hardware, software, and/or firmware. Accordingly, the examples provided are not the only way(s) to implement such systems, methods, apparatus, and/or articles of manufacture.

Additionally, references herein to "example" and/or "embodiment" means that a particular feature, structure, or characteristic described in connection with the example and/or embodiment can be included in at least one example and/or embodiment of an invention. The appearances of this phrase in various places in the specification are not necessarily all referring to the same example and/or embodiment, nor are separate or alternative examples and/or embodiments mutually exclusive of other examples and/or embodiments. As such, the example and/or embodiment described herein, explicitly and implicitly understood by one skilled in the art, can be combined with other examples and/or embodiments.

The specification is presented largely in terms of illustrative environments, systems, procedures, steps, logic blocks, processing, and other symbolic representations that directly or indirectly resemble the operations of data processing devices coupled to networks. These process descriptions and representations are typically used by those skilled in the art to most effectively convey the substance of their work to others skilled in the art. Numerous specific details are set forth to provide a thorough understanding of the present disclosure. However, it is understood to those skilled in the art that certain embodiments of the present disclosure can be practiced without certain, specific details. In other instances, well known methods, procedures, components, and circuitry have not been described in detail to avoid unnecessarily obscuring aspects of the embodiments. Accordingly, the scope of the present disclosure is defined by the appended claims rather than the forgoing description of embodiments.

When any of the appended claims are read to cover a purely software and/or firmware implementation, at least one of the elements in at least one example is hereby expressly defined to include a tangible, non-transitory medium such as a memory, DVD, CD, Blu-ray, and so on, storing the software and/or firmware.

EXAMPLE EMBODIMENTS

Example embodiments include the following:

Embodiment 1

A method comprising: capturing an image of a pinna; based on the image of the pinna, determining a non-linear transfer function which characterizes how sound is transformed at the pinna; and outputting, by a transducer, a signal indicative of one or more audio cues to facilitate spatial localization of sound via the pinna, wherein the one or more audio cues is based on the non-linear transfer function.

Embodiment 2

The method of Embodiment 1, wherein capturing the image of the pinna comprises positioning a mobile device at a given linear distance from the pinna and capturing the image at the given linear distance from the pinna.

Embodiment 3

The method of Embodiment 1 or 2, wherein determining the non-linear transfer function which characterizes how the sound is transformed at the pinna comprises extracting characteristics of one or more features of the pinna based on the image and determining the non-linear transfer function based on the characteristics.

Embodiment 4

The method of any of Embodiments 1-3, wherein capturing the image of the pinna comprises capturing, by an image sensor in an earcup, the image of the pinna.

Embodiment 5

The method of any of Embodiments 1-4, wherein determining a non-linear transfer function which characterizes how sound is transformed at the pinna comprises: comparing the image of the pinna to other images of other pinnas, wherein each image of the other pinnas is associated with a respective non-linear transfer function; determining one of the other images which is closest to the image of the pinna based on the comparison; and identifying the non-linear transfer function as the respective non-linear transfer function associated with the one of the other images.

Embodiment 6

The method of any of Embodiments 1-5, wherein the one or more audio cues indicates one or more of an elevation, distance, and velocity associated with the spatialization of the sound.

Embodiment 7

The method of any of Embodiments 1-6, wherein outputting, by the transducer, one or more audio cues comprises modulating a signal with the non-linear transfer function to produce a modulated signal which defines the one or more audio cues for spatialization of the sound.

Embodiment 8

The method of any of Embodiments 1-7, wherein capturing an image of a pinna comprises capturing, via a mobile device, a plurality of images of a pinna at a plurality of orientations, wherein the plurality of images at the plurality of orientations indicates at least a relative distance between features of the pinna and a depth of features of the pinna.

Embodiment 9

The method of any of Embodiments 1-8, wherein capturing the plurality of images of the pinna comprises moving the mobile device or moving a head to capture the pinna at different orientations.

Embodiment 10

The method of any of Embodiments 1-9, further comprising receiving, by a motion sensor, an orientation of the mobile device, and wherein determining the non-linear transfer function comprises rotating an image of the plurality of images based on the orientation of the mobile device via a rotation matrix.

Embodiment 11

The method of any of Embodiments 1-10, wherein the plurality of images of a pinna comprises a plurality of profiles of the pinna.

Embodiment 12

The method of any of Embodiments 1-11, wherein determining the non-linear transfer function comprises combining the plurality of images to form a multi-dimensional image of the pinna.

Embodiment 13

The method of any of Embodiments 1-12, wherein capturing, via the mobile device held at the plurality of orientations, a plurality of images of the pinna comprises capturing, via the mobile device, a given image in a plane which passes through a left and right ear on a head and which divides the head into two halfs.

Embodiment 14

One or more non-transitory computer readable media comprising program code stored in memory and executable by a processor, the program code to: capture an image of a pinna; based on the image of the pinna, determine a non-linear transfer function which characterizes how sound is transformed at the pinna; and output, by a transducer, a signal indicative of one or more audio cues to facilitate spatial localization of sound via the pinna, wherein the one or more audio cues is based on the non-linear transfer function.

Embodiment 15

The one or more non-transitory machine-readable media of Embodiment 14, wherein the program code to capture the image of the pinna comprises positioning a mobile device at a given linear distance from the pinna and capturing the image at the given linear distance from the pinna.

Embodiment 16

The one or more non-transitory machine-readable media of Embodiment 14 or 15, wherein the program code to capture the image of the pinna comprises capturing, by an image sensor in an earcup, the image of the pinna.

Embodiment 17

The one or more non-transitory machine-readable media of any of Embodiments 14-16, wherein the program code to determine a non-linear transfer function which characterizes how sound is transformed at the pinna comprises: comparing the image of the pinna to other images of other pinnas, wherein each image of the other pinnas is associated with a respective non-linear transfer function; determining one of the other images which is closest to the image of the pinna based on the comparison; and identifying the non-linear transfer function as the respective non-linear transfer function associated with the one of the other images.

Embodiment 18

The one or more non-transitory machine-readable media of any of Embodiments 14-17, wherein the program code to capture the plurality of images of the pinna comprises moving the mobile device or moving a head.

Embodiment 19

The one or more non-transitory machine-readable media of any of Embodiments 14-18, wherein the plurality of images of a pinna comprises a plurality of profiles of the pinna.

Embodiment 20

A system comprising: an audio device; computer instructions stored in memory and executable by a processor to perform the functions of: capturing, by the audio device, an image of a pinna; based on the image of the pinna, determining a non-linear transfer function which characterizes how sound is transformed at the pinna; and outputting, by a transducer of the audio device, a signal indicative of one or more audio cues to facilitate spatial localization of sound via the pinna, wherein the one or more audio cues is based on the non-linear transfer function.

I claim:

1. A method comprising:
capturing, by an image sensor, one or more images of a reference pinna;
based on the one or more images of the reference pinna, determining a head related transfer function (HRTF) which characterizes how sound is transformed by the reference pinna, wherein determining the HRTF comprises inputting the one or more images of the reference pinna captured by the image sensor into a neural network model which outputs the HRTF which characterizes how sound is transformed by the reference pinna; and
outputting, by a transducer, a signal indicative of one or more audio cues to facilitate spatial localization of sound via the reference pinna, wherein the one or more audio cues is based on the HRTF.

2. The method of claim 1, wherein capturing the one or more images of the reference pinna comprises determining, by a proximity sensor, a distance between a mobile device and the reference pinna; and capturing, by the image sensor of the mobile device, the one or more images of the reference pinna when a proximity sensor indicates that the mobile device is at a given linear distance from the reference pinna.

3. The method of claim 1, wherein capturing the one or more images of the reference pinna comprises positioning a mobile device having a camera configured with the image sensor proximate to the reference pinna to capture a video of the reference pinna.

4. The method of claim 1, wherein determining the HRTF comprises extracting characteristics of one or more features of the reference pinna based on the one or more images of the reference pinna.

5. The method of claim 1, wherein capturing the one or more images of the reference pinna comprises capturing, via a mobile device configured with the image sensor, a plurality of images of the reference pinna at a plurality of orientations, wherein the plurality of images of the reference pinna at the plurality of orientations indicates at least a relative distance between features of the reference pinna and a depth of features of the reference pinna.

6. The method of claim 5, wherein capturing the one or more images of the reference pinna comprises combining the plurality of images of the reference pinna to form a multi-dimensional image of the reference pinna; and wherein determining the HRTF comprises inputting the multi-dimensional image into the neural network model.

7. The method of claim 1, wherein the one or more images of the reference pinna is associated with a first individual and the neural network model is fit to a plurality of HRTFs and associated images of pinna associated with second individuals other than the first individual.

8. One or more non-transitory machine-readable media comprising computer instructions stored in memory and executable by a processor, the computer instructions to:
capture, by an image sensor, one or more images of a reference pinna;
based on the one or more images of the reference pinna, determine a head related transfer function (HRTF) which characterizes how sound is transformed by the reference pinna, wherein determining the HRTF comprises inputting the one or more images of the reference pinna captured by the image sensor into a neural network model which outputs the HRTF which characterizes how sound is transformed by the reference pinna; and
output, by a transducer, a signal indicative of one or more audio cues to facilitate spatial localization of sound via the reference pinna, wherein the one or more audio cues is based on the HRTF.

9. The one or more non-transitory machine-readable media of claim 8, wherein the computer instructions to capture the one or more images of the reference pinna comprises computer instructions to determine, by a proximity sensor, a distance between a mobile device and the reference pinna; and capture, by the image sensor of the mobile device, the one or more images of the reference pinna when a proximity sensor indicates that the mobile device is at a given linear distance from the reference pinna.

10. The one or more non-transitory machine-readable media of claim 8, wherein the computer instructions to capture the one or more images of the reference pinna comprises receiving the one or more images of the reference pinna from a mobile device having a camera configured with the image sensor, the image sensor positioned proximate to the reference pinna to capture a video of the reference pinna.

11. The one or more non-transitory machine-readable media of claim 8, wherein the computer instructions to determine the HRTF comprises computer instructions to extract characteristics of one or more features of the reference pinna based on the one or more images of the reference pinna.

12. The one or more non-transitory machine-readable media of claim 8, wherein the computer instructions to capture the one or more images of the reference pinna comprises computer instructions to capture, via a mobile device configured with the image sensor, a plurality of images of the reference pinna at a plurality of orientations, wherein the plurality of images of the reference pinna at the plurality of orientations indicates at least a relative distance between features of the reference pinna and a depth of features of the reference pinna.

13. The one or more non-transitory machine-readable media of claim 12, wherein the computer instructions to capture the one or more images of the reference pinna comprises computer instructions to combine the plurality of images of the reference pinna to form a multi-dimensional image of the reference pinna; and wherein the computer instructions to determine the HRTF comprises computer instructions to input the multi-dimensional image into the neural network model.

14. The one or more non-transitory machine-readable media of claim 8, wherein the one or more images of the reference pinna is associated with a first individual and the neural network model is fit to a plurality of HRTFs and associated images of pinna associated with second individuals other than the first individual.

15. A system comprising:
a mobile device having a camera, the camera configured with an image sensor;
computer instructions stored in memory and executable by a processor to perform functions of:
capturing, by the image sensor of the camera, one or more images of a reference pinna;
based on the one or more images of the reference pinna, determining a head related transfer function (HRTF) which characterizes how sound is transformed by the reference pinna, wherein determining the HRTF comprises inputting the one or more images of the reference pinna captured by the image sensor into a neural network model which outputs the HRTF which characterizes how sound is transformed by the reference pinna; and
outputting a signal indicative of one or more audio cues to facilitate spatial localization of sound via the reference pinna, wherein the one or more audio cues is based on the HRTF.

16. The system of claim 15, wherein the computer instructions to capture the one or more images of the reference pinna comprises receiving the one or more images of the reference pinna from the mobile device having the camera, the image sensor of the camera positioned proximate to the reference pinna to capture a video of the reference pinna.

17. The system of claim 15, wherein the computer instructions to determine the HRTF comprises computer instructions to extract characteristics of one or more features of the reference pinna based on the one or more images of the reference pinna.

18. The system of claim 15, wherein the computer instructions to capture the one or more images of the reference pinna comprises computer instructions to capture a plurality of images of the reference pinna at a plurality of orientations, wherein the plurality of images of the reference pinna at the plurality of orientations indicates at least a relative distance between features of the reference pinna and a depth of features of the reference pinna.

19. The system of claim 18, wherein the computer instructions to capture the one or more images of the reference pinna comprises computer instructions to combine the plurality of images of the reference pinna to form a multi-dimensional image of the reference pinna; and wherein the computer instructions to determine the HRTF comprises computer instructions to input the multi-dimensional image into the neural network model.

20. The system of claim 15, wherein the one or more images of the reference pinna is associated with a first individual and the neural network model is fit to a plurality of HRTFs and associated images of pinna associated with second individuals other than the first individual.

21. The method of claim 1, wherein inputting the one or more images of the reference pinna captured by the image sensor into the neural network model which outputs the HRTF comprises the neural network model predicting the HRTF based on the one or more images of the reference pinna captured by the image sensor.

22. The one or more non-transitory machine-readable media of claim 8, wherein the computer instructions to input the one or more images of the reference pinna captured by the image sensor into the neural network model which outputs the HRTF comprises computer instructions for the neural network model to predict the HRTF based on the one or more images of the reference pinna captured by the image sensor.

23. The system of claim 15, wherein the computer instructions to input the one or more images of the reference pinna captured by the image sensor into the neural network model which outputs the HRTF comprises computer instructions for the neural network model to predict the HRTF based on the one or more images of the reference pinna captured by the image sensor.

* * * * *